US009820656B2

(12) United States Patent
Olivier

(10) Patent No.: US 9,820,656 B2
(45) Date of Patent: Nov. 21, 2017

(54) PERSONALIZED NUTRITIONAL AND WELLNESS ASSISTANT

(75) Inventor: Laurence Richard Olivier, Alpharetta, GA (US)

(73) Assignee: LifeQ Global Limited, Dublin (IE)

( * ) Notice: Subject to any disclaimer, the term of this patent is extended or adjusted under 35 U.S.C. 154(b) by 296 days.

(21) Appl. No.: 14/128,675

(22) PCT Filed: Jul. 6, 2012

(86) PCT No.: PCT/US2012/045657
§ 371 (c)(1),
(2), (4) Date: Dec. 23, 2013

(87) PCT Pub. No.: WO2013/009589
PCT Pub. Date: Jan. 17, 2013

(65) Prior Publication Data
US 2014/0128691 A1    May 8, 2014

Related U.S. Application Data

(60) Provisional application No. 61/614,191, filed on Mar. 22, 2012, provisional application No. 61/505,877, filed on Jul. 8, 2011.

(51) Int. Cl.
*A61B 5/02*      (2006.01)
*A61B 5/0205*   (2006.01)
(Continued)

(52) U.S. Cl.
CPC .......... *A61B 5/0205* (2013.01); *A61B 5/0022* (2013.01); *A61B 5/0082* (2013.01);
(Continued)

(58) Field of Classification Search
CPC ... A61B 5/0082; A61B 5/0833; A61B 5/0836; A61B 5/087; A61B 5/14551; A61B 5/02438; A61B 5/682
(Continued)

(56) References Cited

U.S. PATENT DOCUMENTS 5,101,825 A    4/1992  Gravenstein et al.
5,363,857 A    11/1994 Howard
(Continued)

FOREIGN PATENT DOCUMENTS

CN       1326328 A    12/2001
CN      101801261     8/2010
(Continued)

OTHER PUBLICATIONS

Second Chinese Office Action dated Aug. 17, 2015 with English translation; 19 pages.
(Continued)

*Primary Examiner* — Paula J Stice
(74) *Attorney, Agent, or Firm* — Smith Gambrell & Russell LLP

(57) ABSTRACT

The invention pertains to the establishment, implementation and management of a personalized information system pertinent to a user's general health, wellness and/or sport performance. Disclosed is a system capable of transcutaneous measurement of a subject including at least one light source, at least one light detector, and at least one component for generating or storing at least one value of $VCO_2$ or at least one value of $VO_2$ from the detected signal. Further, disclosed is a portable device for analyzing the composition of the respired gasses of a subject including at least one air flow conduit through which the subject can inspire or expire air through the body of the device, at least one sampling portal, an oxygen sensor, and at least one flow sensor. A dual-battery system is also provided by which an uninterrupted power supply can be provided for electronic components.

34 Claims, 10 Drawing Sheets

(51) Int. Cl.

| | | |
|---|---|---|
| *A61B 5/083* | (2006.01) | |
| *A61B 5/087* | (2006.01) | |
| *A61B 5/00* | (2006.01) | |
| *A61B 5/22* | (2006.01) | |
| *G06Q 50/22* | (2012.01) | |
| *A61B 5/08* | (2006.01) | |
| *A61B 5/1455* | (2006.01) | |
| *A61B 5/024* | (2006.01) | |
| *A61B 5/053* | (2006.01) | |
| *H02J 9/06* | (2006.01) | |

(52) U.S. Cl.
CPC .............. *A61B 5/082* (2013.01); *A61B 5/087* (2013.01); *A61B 5/0833* (2013.01); *A61B 5/0836* (2013.01); *A61B 5/14551* (2013.01); *A61B 5/222* (2013.01); *A61B 5/4869* (2013.01); *A61B 5/7235* (2013.01); *G06Q 50/22* (2013.01); *A61B 5/02438* (2013.01); *A61B 5/053* (2013.01); *A61B 2503/10* (2013.01); *A61B 2560/0214* (2013.01); *A61B 2560/0223* (2013.01); *A61B 2560/0431* (2013.01); *H02J 9/06* (2013.01)

(58) Field of Classification Search
USPC ................................................. 600/300–301
See application file for complete search history.

(56) References Cited

U.S. PATENT DOCUMENTS

| | | | |
|---|---|---|---|
| 5,369,802 | A | 11/1994 | Murray |
| 6,475,158 | B1 | 11/2002 | Orr et al. |
| 6,517,496 | B1 | 2/2003 | Mault |
| 6,790,178 | B1 | 9/2004 | Mault et al. |
| 6,859,658 | B1 | 2/2005 | Krug |
| 6,936,376 | B2 | 8/2005 | Plumadore |
| 6,955,650 | B2 | 10/2005 | Mault et al. |
| 7,897,109 | B2 | 3/2011 | Labuda et al. |
| 2001/0034479 | A1 | 10/2001 | Ring et al. |
| 2002/0173728 | A1 | 11/2002 | Mault |
| 2003/0006527 | A1 | 1/2003 | Rabolt et al. |
| 2003/0065273 | A1 | 4/2003 | Mault et al. |
| 2003/0065274 | A1 | 4/2003 | Mault |
| 2003/0149349 | A1 | 8/2003 | Jensen |
| 2004/0186390 | A1 | 9/2004 | Ross et al. |
| 2005/0225914 | A1 | 10/2005 | King |
| 2006/0115689 | A1 | 6/2006 | Lee |
| 2006/0253010 | A1 | 11/2006 | Brady et al. |
| 2008/0004541 | A1 | 1/2008 | Grane |
| 2008/0161710 | A1 | 7/2008 | Gunneson et al. |
| 2008/0275317 | A1* | 11/2008 | Cho ................... A61B 5/0059 600/310 |
| 2009/0024013 | A1 | 1/2009 | Soller |
| 2011/0009764 | A1 | 1/2011 | Lanier et al. |
| 2011/0144465 | A1 | 6/2011 | Shults et al. |

FOREIGN PATENT DOCUMENTS

| | | |
|---|---|---|
| CN | 101801261 A | 8/2010 |
| EP | 2 667 768 | 12/2013 |
| EP | 2667768 A2 | 12/2013 |
| JP | 2009-192118 | 7/1997 |
| JP | 2009192118 | 7/1997 |
| JP | 2003-511143 | 3/2003 |
| JP | 2003511143 | 3/2003 |
| JP | 2003-190123 | 7/2003 |
| JP | 2003-284774 | 10/2003 |
| JP | 2005-52385 | 3/2005 |
| JP | 2005-052385 | 3/2005 |
| JP | 2006-314800 | 11/2006 |
| JP | 2010-512953 | 4/2010 |
| JP | 2010512953 | 4/2010 |
| JP | 2010-533514 | 10/2010 |
| WO | WO 01/26547 | 4/2001 |
| WO | WO2009048659 | 4/2009 |

OTHER PUBLICATIONS

Office Action issued by the Mexican Patent Office dated Mar. 22, 2016 (6 pages).
Partial supplementary European Search Report issued for European Patent Application No. 12811212.5 dated Dec. 12, 2014; 7 pages.
European Search Report issued by the European Patent Office dated Apr. 28, 2015, 18 pages.
First Office Action issued by the Chinese Patent Office dated Jan. 20, 2015; 8 pages.
Saalasti, S., "Neural Networks for heart rate times series analysis," University of Jyvaskyla, Finland, 2003, 194 pages.
Uth, et al., "Estimation of VO2max from the ration between HRmax and HRrest-the heart rate method," European Journal of Applied Physiology, 2004, 5 pages.
Office Action released by the Singapore Patent Office dated Feb. 2, 2015, 12 pages.
Patent Examination Report No. 1 released by the Australian Patent Office dated Dec. 14, 2015; 3 pages.
Written Opinion released by the Singapore Patent Office dated Jul. 22, 2015, 12 pages.
Second Office Action released for Mexican Patent Application No. MX/a/2014/000289 dated Aug. 19, 2016 (8 pages).
Korean final rejection released for Korean Patent Application No. 2014-7002701 dated Sep. 20, 2016 (3 pages).
Communication pursuant to Article 94(3) issued by the European Patent Office for European Patent Application No. 12811212.5 dated Oct. 4, 2016; 7 pages.
Office Action issued by the Japanese Patent Office dated Oct. 21, 2016 (17 pages).
Official Action released for Canadian Patent Application for Canadian Application No. 2,839,141 dated Jul. 5, 2016 (3 pages).
Eurasian Official Notification with English translation dated Mar. 25, 2016 (4 pages).
Extended European Search Report issued by the European Patent Office dated Apr. 29, 2016 (11 pages).
Korean Notice of Grounds for Rejection issued by the Korean Patent Office dated Apr. 20, 2016 (15 pages).
Third Office Action issued by the Chinese Patent Office dated Apr. 18, 2016 (24 pages).
Canadian Office Action issued for Canadian Patent Application No. 2,839,141 dated May 29, 2017, 3 pages.
European Communication pursuant to Article 94(3) EPC released by the European Patent Office dated Mar. 9, 2017; 7 pages.
First Office Action issued by the Chinese Patent Office dated Dec. 28, 2016 for corresponding Chinese Patent Application No. 2015101978228; 18 pages.
Office Action issued by the Israel Patent Office dated Jan. 2, 2017 for corresponding Israel Patent Application No. 229885; 5 pages.
Non-final Office Action issued by the U.S. dated Jan. 25, 2017 for corresponding U.S. Appl. No. 15/080,789 (30 pages).
Japanese Office Action released for Japanese Patent Application No. 2016-122378 dated Jun. 16, 2017; 16 pages.
Japanese Office Action released for Japanese Patent Application No, 2016-122378 dated Jun. 16, 2017; 16 pages.
Japanese Notice of Final Rejection issued by the Japanese Patent Office dated Aug. 22, 2017 for corresponding Japanese Application No. 2014-519311; 10 pages.
Korean Notice of Grounds for Rejections issued by the Korean Patent Office dated Sep. 6, 2017 for corresponding Korean Patent Office No. 10-2016-7016488; 6 pages.

* cited by examiner

Viewed From the Front

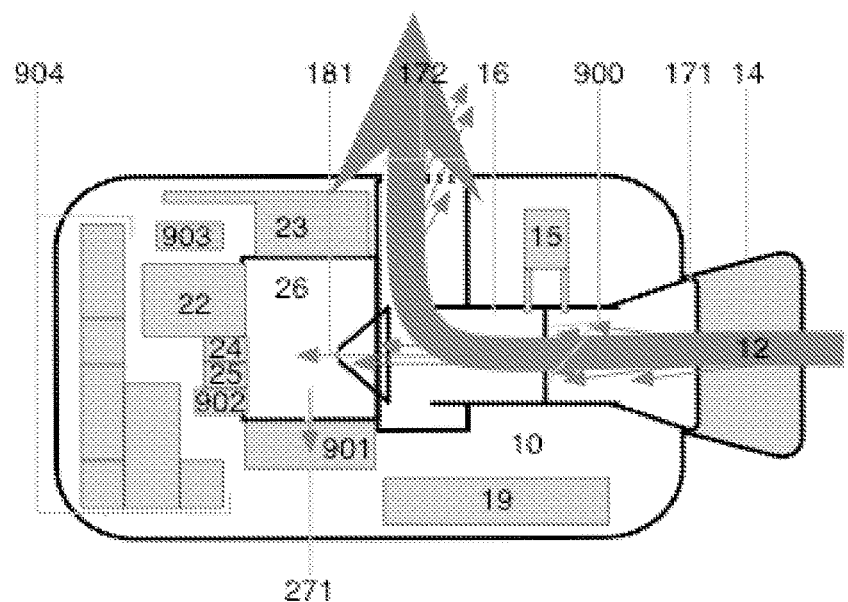
Figure 9a: Air Flow Dynamics generated by an exhalation.
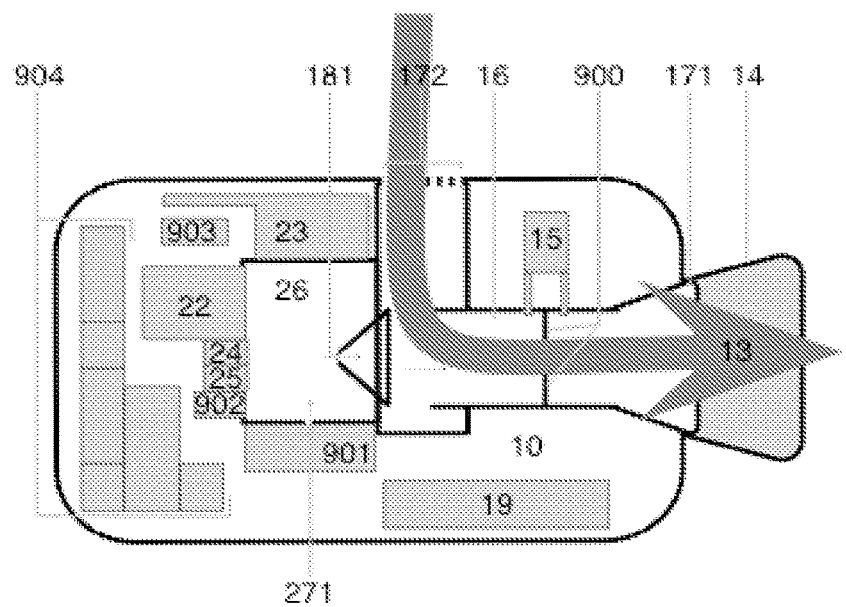
Figure 9b: Air Flow Dynamics generated by an inhalation.

PERSONALIZED NUTRITIONAL AND WELLNESS ASSISTANT

CROSS-REFERENCE TO RELATED APPLICATION

The present patent application claims the benefit of priority to U.S. Provisional Patent Application No. 61/505,877, filed Jul. 8, 2011, and U.S. Provisional Patent Application No. 61/614,191, filed Mar. 22, 2012, both of which are incorporated herein by reference in their entirety.

FIELD OF THE INVENTION

The invention pertains to the field of health, wellness, and sport performance with particular bearing on the use of portable devices to provide continuous real-time and long-term metabolic feedback to a user. In one embodiment, the present invention may conduct simultaneous evaluation of such data to provide real-time personalized nutritional- and/or exercise guidance to the user in order to promote his/her progress towards (or maintenance of) a personal health, wellness and/or sport performance goal. The invention may also be used for the application of such metabolic, physiological, mood and/or behavior data for purposes of scientific and/or clinical research, and general consumer application. The invention may implement such data to motivate users to achieve personal health, wellness, and/or sport performance goals by using personalized user data in a social networking and/or social gaming environments. The measuring technologies utilized may, in one embodiment, relate to the fields of indirect calorimetry and transcutaneous spectrophotometry.

BACKGROUND OF THE INVENTION

The onset of industrialization and the technological era has had tremendous implications for the human diet and the physical demands that we make of our bodies on an everyday basis. Instead of having to expend energy to cultivate homegrown low calorie food resources, vast quantities of people in developed and developing countries are now only a supermarket or fast food chain away from a variety of over-the-counter calorie-dense meals. In addition to this, the largest proportion of these people spend the majority of their waking hours in sedentary position—either pursuing an office job, watching television, playing computer games, reading or socializing (2010 American Time Use Survey and the 2007-2009 Canadian Health Measures Survey).

Unfortunately, the human body is not designed for such a "high calorie intake—low calorie expenditure" lifestyle, and the abundance of serious metabolic disorders characteristic of modern societies (e.g. obesity, diabetes, metabolic syndrome, cardiovascular disease, etc.) reflects the detriments of the modern human's lifestyle. According to the 2009 Global Health Risks report (WHO, 2009) four of the five leading global risks for mortality pertain to metabolic abnormalities, these being high blood pressure (accounting for 13% of mortalities), high blood glucose (6%), physical inactivity (6%) and being overweight or obese (5%). At the same time, six of the eight risk factors accounting for the majority (61%) of cardiovascular mortalities are symptomatic of the modern lifestyle (i.e. high blood pressure, high body mass index, high cholesterol, high blood glucose, low fruit and vegetable intake, and physical inactivity). Although these surveys provide a clear and uncomplicated picture of the most critical areas that need to be addressed to improve the health and life expectancy of humanity, positive changes are rarely observed.

Most people do realize the importance of regular exercise to maintain or improve their general health, yet their inability to realistically observe and gauge their own behavior impedes their achievement of personal health goals. Statscan, for instance, recently reported that 50% of Canadians reported that they regularly participated in a minimum of 180-210 minutes of exercise per week, while in reality only 15% achieved even the minimum recommendation of 150 minutes a week. Even more pronounced is the inability to realistically observe and gauge one's own nutritional condition (low blood sugar levels, for instance, only manifests itself as rather subjective experiences of dizziness, hunger pangs, cravings and/or mood swings, while indicators of high blood sugar levels are virtually non-existent), quality of sleep or level of stress. With these shortcomings in mind, it is hardly a surprise that most modern human beings are not able to achieve and maintain their personal health, wellness and/or sport performance goals—even if they go at it with the best of intentions.

Modern societies have gymnasiums and dietary organizations that provide guidance and support to those aiming to improve their general health and wellbeing. Although largely successful, low frequency contact sessions are a typical feature of such enterprises and members often regress to their former lifestyles when their contracts reach full term. Virtually none, if any, of these bodies have the capacity to provide their members with real-time motivators and feedback about the progress that they are making with regards to their personal dietary or fitness goals, and they are even less adapted to provide them with much-needed real-time nutritional and exercise guidance and support.

Ironically, the very same phenomenon (technology) that has brought such unhealthy lifestyles upon us is also able to provide solutions to some of our troubles: Instantaneous information about our metabolic rates can be obtained through the use of a wide variety of metabolic measuring devices (e.g. ReeVue and MetaCheck (Korr), MedGem® & BodyGem® (Microlife), Quark RMR and Fitmate (COSMED), a Douglas Bag, a metabolic chamber, etc.), while knowledge about our body composition (i.e. the ratio of lean body mass to body fat mass) can be obtained through a range of modern techniques and technologies (e.g. isotope dilution, magnetic resonance imaging, hydrostatic weighing, computed tomography, neutron activation, dual energy X-ray absorptiometry (DEXA), BodyMetrix ultrasound, BodPod (LMi), Tanita, skin fold measurements, BMI calculations, and the use of equations such as the Harris-Benedict equation in combination with the Katch-McArdle equation). Although not essential for general health improvement in itself, body composition has been shown to be an important determinant of our risk of developing diabetes, high blood pressure, high cholesterol, cardiovascular disease, hormone imbalances etc. and knowledge of our personal body compositions can be extremely helpful in aiding us to take the right decisions about our dietary and exercise routines. At the same time, wearable energy tracking devices have recently become exceptionally popular for the provision of information about our daily calorie expenditure (e.g. Fitbit, Bodybugg® (BodyMedia), Nike+ FuelBand, Basis watch, MotoActv (Motorola), myTREK (Scosche), Forerunner® (Garmin), etc.), while a plethora of mobile phone applications exist that allow us to log and track our approximate energy expenditure and/or energy consumption (e.g. Fitocracy, Runkeeper, Endomondo, Cardiotrainer, Adidas MiCoach, intelli-Diet, DailyBurn, NutriTiming, etc.). Other self-quantification devices and applications aspire to track sleep patterns (e.g. Zeo), mood (e.g. HealthyPlace, Mood 24/7) and stress levels (e.g. Basis watch, Stress Tracker, etc.). Finally, the recent introduction of motion-sensing computer games (e.g. Nintendo's Wii) to the market provides many people with a significant motivation to improve their personal fitness levels, mainly as a result of the entertainment factor provided by the instantaneously relayed user-motions to an avatar in a game.

All techniques and technologies considered, however, the presence of innovations capable of highly accurate real-time evaluation of a person's every day energy expenditure, energy uptake (as opposed to intake) and nutritional state (i.e. which macronutrient resource the user is utilizing as metabolic fuel at any given moment) remains glaringly absent from the market. Current wearable real-time measuring devices make use of variables such as motion sensing (accelerometers), heart rate, galvanic skin response and skin temperature from which real-time energy expenditure levels can be estimated. Unfortunately, most of these devices provide only moderately accurate and non-user specific calorimetric output.

An arena in which these shortcomings are of particular importance is in the training and shaping of professional athletes. Real-time physiological monitoring and shaping of athletes are becoming essential for elite athletes to ensure maximum performance and to keep stretching the envelope of achievements and world records. Managers, coaches and trainers of elite athletes increasingly rely on cutting edge technologies to condition and shape athletes, or to guide athletes while competing. While GPS and heart rate monitoring have become commonplace in this environment, increased attention is being placed on the combination of nutrition and exercise regimes for general conditioning, pre-competition priming, and during competitions to achieve maximum performance. To this end, no technologies that can provide accurate real time monitoring of metabolic data exist that can be used to optimize the combination of nutrition and exercise during general conditioning, pre, and during competitions. To date, visual monitoring technologies are most commonly applied in addition to GPS and heart rate sensing to provide real time data for managing the performance of athletes, none of which adequately satisfying the increasing needs to integrate nutrition uptake and expenditure into the above equations.

In addition, while almost all of the wearable innovations mentioned above suffer shortcomings that result in unsatisfactory or inaccurate feedback to the user, hardly any of them provide the user with a real-time estimate of the user's personal respiratory quotient (RQ). The importance of the RQ-value lies in its ability to elucidate the main energy source that the body is utilizing at a given moment in time for its metabolic activities (i.e. the RQ-vale elucidates what type of energy resource the user is combusting at the instant in which the respiratory quotient is measured). This is possible because the RQ-value represents the ratio of $CO_2$ molecules produced per molecule of $O_2$ consumed during the combustion process, and as such reflects the molecular structure of the combusting material (carbohydrates, for instance, are more oxidized than fat molecules—hence combustion of carbohydrates result in higher RQ-values if compared to combustion of fats). Accurate determination of real-time RQ-values can be invaluable to users suffering from metabolic deviations (RQ-values close to 0.7 are often indicative of catabolic metabolism and diabetes, while high glycemic index diets are characterized by RQ-values of close to 1.0). At the same time, the value can be extremely useful to those that would simply like to maintain proper metabolic homeostasis.

Human metabolism is typically characterized by RQ-values within the range 0.7 (characteristic of a fat-only combustion) and 1.0 (characteristic of highly oxidized carbohydrate combustion). Other known RQ-values include those for ethanol combustion (0.67), protein combustion (0.82), mixed substrate combustion (0.85), and lipid synthesis (1.0-1.2). Table 1 shows the relationship between the energy produced from a proportional combination of two sub-sets of food, and the corresponding RQ-values:

TABLE 1

| Dietary Composition | | Energy | |
|---|---|---|---|
| % Carbohydrate | % Fat | (Kcal/L $O_2$) | RQ |
| 0 | 100 | 4.69 | 0.71 |
| 16 | 84 | 4.74 | 0.75 |
| 33 | 67 | 4.80 | 0.8 |
| 51 | 49 | 4.86 | 0.85 |
| 68 | 32 | 4.92 | 0.9 |
| 84 | 16 | 4.99 | 0.95 |
| 100 | 0 | 5.05 | 1 |

The accuracy of real-time metabolic data (such as real-time energy expenditure and real-time RQ) can be increased by calibrating measuring devices with a user's resting metabolic parameters (obtainable through indirect calorimetry). Such data can be obtained from indirect calorimetry devices that make use of a user's true resting respiratory quotient (RQ) to determine his/her metabolic rate. All handheld/home-user calorimetric devices currently on the market, however, make use of a generic RQ value (usually 0.85) which does not provide this capacity. For example, in U.S. Pat. No. 4,917,108, Mault describes a device that is able to determine the oxygen consumption rate of a user through direct measurement of the amount of oxygen in inhaled and exhaled air. $CO_2$ measurements are not included in the design, however, and the device relies on an assumed respiratory quotient value to calculate the (consequently biased and inaccurate) metabolic rates of users. In an improved design (U.S. Pat. Nos. 5,179,958 and 6,468,222), Mault determines the $CO_2$ production rate of the user by measuring the absorption of infrared light when shined through inhaled and exhaled air. This type of $CO_2$ sensor has a rapid response time, thus allowing accurate characterization of every breath during breath-by-breath gas composition analysis (i.e. the device permits gas analysis directly inside the air flow pathway and does not include a sampling chamber for gas accumulation, or the use of more affordable slow gas analysis sensors—as described for the "Regular Interval Calibration Unit" (RICU) of the current invention, described in further detail below). Besides being expensive as a result of the use of expensive rapid response type sensors, the device is suitable for discontinuous use only, and can only provide real-time feedback about the user's respiratory quotient or metabolic rate during the period in which the user is actually breathing into the device (this as opposed to the "Continuous Real-time Monitoring Device" (CrtMD) described in the current invention, below).

Similarly, affordable techniques for body composition analysis provide generalized and inaccurate results, while those capable of accurate body composition determination invariably involve costly, cumbersome, and time-consuming procedures as well as the skills of highly trained technicians to operate the equipment and analyze results. Moreover, accurate innovations often require the use of large, immobile equipment (mostly situated in a clinical or laboratory setting), which means that very few people can have regular access to accurate knowledge about their personal body composition. A person's body composition (i.e. body fate percentage) can also be calculated from his/her resting metabolic rate if his/her weight is known. If the user has an atypical metabolic profile, however, this calculation could be erroneous. It is therefore recommended that the calculated value be validated against another method of body composition analysis (e.g. bioelectrical impedance). Thus, an indirect calorimeter, as described below with respect to the present invention, can serve a dual function: (i) to estimate the resting metabolic values of a user—useful for calibration of a real-time metabolic measuring device, and (ii) to estimate a user's body composition. At present, Microlife's MedGem® and BodyGem® seem to be the only hand-held indirect calorimeters on the market—and neither of these makes use of bioelectrical impedance to augment body composition calculations from the resting metabolic rate data. These devices, however, measure the $O_2$ concentrations of inspired and expired air directly in the air flow pathway on a breath-by-breath basis. To do this requires the use of oxygen sensors with a fast response time (100 msec or less, e.g. thin-film fluorescence-based oxygen sensors) and simultaneous measurement of the air flow rate by similarly fast ultrasonic flow meters. The costs of these quick response sensors, however, render these products prohibitively expensive and inaccessible to the largest part of society.

The potential for health improvement through real-world/virtual-world integration is clearly illustrated by the popularity of the recently introduced motion-sensing computer games. Nonetheless, the notion of informed health improvement and/or maintenance has not yet been realized in the field. Hardly any of these games provide detailed feedback or insight into the short- and long term benefits of playing them, and none of them make use of user-specific real-time physiological or metabolic parameters (e.g. real-time respiratory quotient (rtRQ), real-time energy expenditure (rtEE), real-time energy uptake (E-uptake) and current body composition (CBC)) to control or provide qualities to the user's avatar. Despite the availability of all of these techniques and technologies, the vast majority of people remain ineffective at taking control of their own health and the need for an affordable innovation capable of accurate real-time feedback about the energy uptake, metabolic rate and nutritional state of its user cannot be overstated.

LED-technology has been of major importance in reducing the costs and size of modern physiology monitoring devices. Patent documents pertaining to the measurement of physiological parameters through the use of LED-technology abound (e.g. heart rate (US Patent Application 2006/0253010, U.S. Pat. No. 7,470,234), oxygen saturation (U.S. Pat. No. 2,706,927, U.S. Pat. No. 4,653,498), hemoglobin concentration (U.S. Pat. No. 5,413,100) and tissue pH (U.S. Pat. No. 5,813,403)). However, its application to human metabolism remains incomplete: To date there does not exist an LED-based real-time physiological measuring device that can estimate real-time energy uptake and/or real-time metabolic fuel utilization. There also does not exist an application in which the accuracy of an LED-based real-time calorimetry device can be increased through calibration with a user's resting physiological parameters as measured by a standard open- or closed-circuit indirect calorimeter. More generally, however, the strategy of calibrating a wearable physiological measuring device (e.g. Garmin or Polar heart rate monitor, Fitbit, etc.) by means of a technology based on absolute indicators of metabolic rate (such as the indirect calorimeter of the present invention, which is described in further detail below) is not known in the art.

SUMMARY OF THE INVENTION

In one embodiment, the present invention overcomes problems and disadvantages associated with current metabolic measurement techniques and technologies through the introduction of two novel affordable and integrateable calorimetry instruments capable of accurate, real-time measurement, analysis and monitoring of metabolic parameters, including the instantaneous respiratory quotient (RQ). More specifically, the present invention describes a novel technology useful for creation of an affordable, portable, indirect calorimeter with the capacity to: (i) estimate the resting metabolic values of a user, and (ii) estimate a user's body composition. The present invention also describes a novel LED-based real-time physiological measuring device that can estimate real-time energy expenditure, real-time metabolic fuel utilization (i.e. what type of macronutrient the user's body is utilizing as metabolic fuel at a given instance in time), real-time energy uptake, sleep tracking, stress tracking, mood tracking, and the like. The present invention also includes a novel methodology by which the data obtained from the above devices are integrated to calibrate the LED-based real-time measuring device through the use of the user's resting metabolic values. In yet another embodiment, the present invention also introduces the concept of a real-time user support system capable of real-time analysis of the user's nutritional state, energy expenditure levels and his/her progress towards a health/performance/wellness goal (e.g. weight loss, increasing fitness levels, reducing overtraining, improving sleep quality, reducing stress levels, etc.) with simultaneous provision of real-time guidance with regards to dietary and exercise decisions. The present invention may integrate user information, such as (but not limited to real-time energy expenditure), with social networking/gaming and other social interaction environments. In addition, the metabolic and physiological data generated by the present invention may have vast other scientific and clinical relevance and applications. The present invention may provide the added benefit that, in contrast to most available technologies that approximate various measurements, a user-friendly environment may be provided requiring minimal user-input, while providing maximum information output, thereby reducing the complexity of its usage to the absolute minimum.

A first aspect of the current invention may provide a personalized information system pertinent to a user's general health, wellbeing and/or sport performance. The information network is embodied in a Personalized Nutritional and Wellness Assistant, which comprises in one embodiment the use of the second and third aspects of the current invention (described further below) in conjunction with other modern information technologies (e.g. web-based servers, smartphone applications, social networks, gaming environments, etc.) to provide the user with real-time and/or long-term feedback with regards to his/her metabolic condition, as well as with real-time and/or long-term guidance with regards to behavior favorable to the maintenance or improvement of the user's metabolic condition. Of primary importance is the network's capacity to determine the real-time nutritional state, the energy uptake and/or energy expenditure level of the user, and its subsequent provision of real-time personalized nutritional- and exercise guidance to the user, in order to advance his/her efficiency at achieving and maintaining his/her specific health, wellness and/or sport performance goal(s). The Personalized Nutritional and Wellness Assistant may be designed to evaluate manual input, measured and/or calculated data in relation to the user's personal health, wellness and/or sport performance goal(s), in order to provide the user with real-time and long-term feedback about his/her progress with regards to these goal(s). The Personalized Nutritional and Wellness Assistant may also incorporate a moving or rolling average to act as a general trend indicator and communicate information to the user with regards to his/her progress towards his/her goal through color coding. In addition, the Personalized Nutritional and Wellness Assistant may provide the user with personalized motivators and incentives in order to advance his/her progress with regards to his/her personal health, wellness and/or sport performance goal(s). Furthermore, the Personalized Nutritional & Wellness Assistant is able to discover, inform and/or educate a user about patterns in his/her behavior (or physiology) that trigger unwanted and/or desirable physiological (or behavioral) responses by continuously and/or intermittently considering all the system variables (i.e. user inputs, data obtained from the second and third aspects of the current invention, etc.). Given the user's consent, the above mentioned 'discovery' capacity of the Personalized Nutritional & Wellness Assistant could also be utilized (as is, or in conjunction with other data such as geological data (e.g. GPS), behavioral data (i.e. online social interaction and purchase behavior), genetic data, etc.) to discover parameters suitable for health risk analysis, sport performance predictions, personalized advertising and other applications. As such, the Personalized Nutritional & Wellness Assistant provides a wealth of information that could prove highly valuable for clinical and/or non-clinical research and/or applications. The Personalized Nutritional & Wellness Assistant may also include a novel and unique dimension to the functionality of the second and third aspects of the current invention (described in further detail below).

A second aspect of the present invention provides a non-invasive wearable device capable of continuous, accurate measurement of the instantaneous metabolic condition of the user while also providing more general features such as time output, accelerometry, geolocation data logging, etc. The present invention may make use of a unique light spectrum and data analysis methodology to obtain highly accurate real-time metabolic measurements. This second aspect of the present invention has the ability to provide 24/7 uninterrupted feedback about metabolic parameters that were previously not determinable without the use of an indirect calorimeter (i.e. a device through which the user must breathe) or metabolic chamber. Parameters of importance in this regard may include, but are not limited to, the real-time respiratory quotient (rtRQ), real-time energy uptake (rtEU) and real-time energy balance (rtEB). In addition, the second aspect of the present invention provides more accurate metabolic rate data (i.e. energy expenditure data) than most wearable calorimetric devices—this because it differs from other wearable calorimetric devices in its direct measurement of the RQ-value (as opposed to utilizing a predetermined average RQ-value, e.g. 0.83). Direct determination of the RQ-value provides the second aspect of the present invention with the capacity to continuously determine even more metabolic parameters of importance in real time (including, but not limited to, the type of macronutrient the body is utilizing as metabolic fuel at a given instant in time, Fat Free Mass (FFM), Current Body Composition (CBC), etc.) when used in conjunction with mathematical modeling and computational systems biology.

A third aspect of the present invention provides a small portable, non-invasive unit with the capacity to analyze the composition, flow rate and/or volume of a subject's respired gasses. While indirect calorimetry may be one purpose of the unit, it may also include sensors that permit measurement of the subject's bioelectrical impedance (from which the subject's body composition can be calculated) and/or heart rate. In contrast to most comparable technologies, the design of this third aspect of the invention is compact (i.e. small enough to be held in one hand) and permits passive gas sampling (as a result of design-driven fluid dynamics). Another feature of the third aspect of the current invention is its implementation of slow oxygen and/or carbon dioxide sensors—this as a result of its unique sampling mechanism. The combined use of slow sensors and a passive sampling mechanism provides the unit with the capacity to measure the oxygen consumption rate ($VO_2$) and the carbon dioxide production rate ($VCO_2$) of the subject with great accuracy, but at a greatly reduced cost. In addition, the third aspect of the present invention provides a capacity for regular interval calibration of the second aspect of the invention in order to continuously improve the accuracy of the latter's readings. In addition, the third aspect of the present invention provides a capacity for regular interval calibration of the second aspect of the invention in order to continuously improve the accuracy of the latter's readings.

A fourth aspect of the present invention provides a dual battery system, with the capacity to provide an uninterrupted power supply to the electronic components of the second aspect of the current invention (or any other electronic device not specifically described in this patent specification) when the battery/electrochemical cell has to be replaced.

A fifth aspect of the present invention pertains to a process which enables one to compare signals of differing intensity(s) and/or wavelength(s) and/or orientation(s) as detected by a signal detecting module (i.e. and algorithm for automatic gain/level adjustments)—thus enabling smooth and optimal graphic representation of such signals on a graphic interface.

While the present invention is described in detail with reference to various embodiments, it will be appreciated that the present invention is not limited to the embodiments described herein only, and that various modifications may be made without departing from the scope of the invention defined in the accompanying claims.

BRIEF DESCRIPTION OF THE DRAWINGS

The preferred embodiment of the invention will now be described, by way of example only, with reference to the accompanying representations in which:

FIG. 9 depicts one embodiment of the design of the air flow conduit and sampling portal of the RICU by means of which fluid dynamics conductive for passive sampling of expired air is generated.

DETAILED DESCRIPTION OF THE INVENTION

Figure 1:
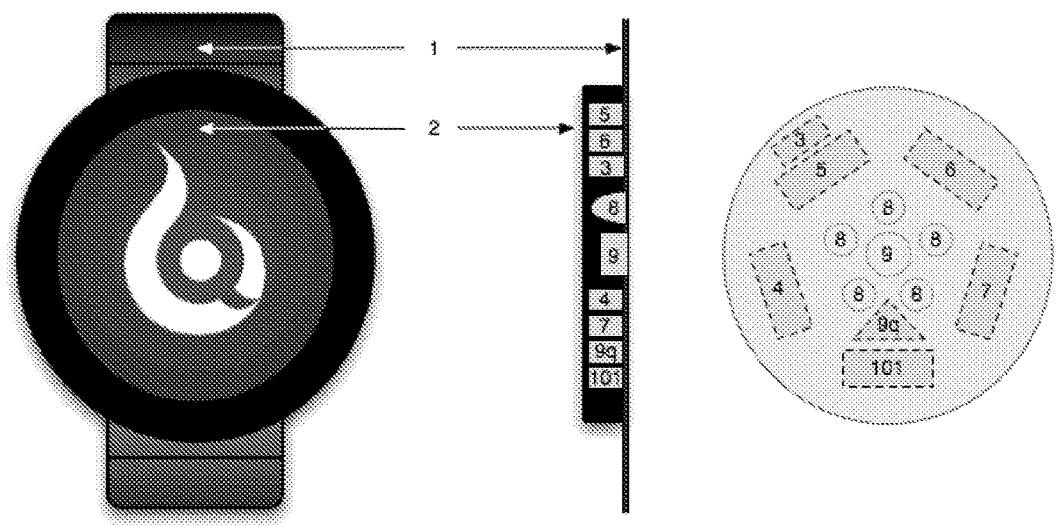
FIG. 1 is a schematic representation of an exemplary embodiment of the "Continuous Real-time Monitoring Device" (CrtMD) used for measuring and relaying physiological and/or metabolic parameter data of a subject in real time.

The following detailed description and appended drawings describe and illustrate various aspects of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical.

Before the present methods and systems are disclosed and described, it is to be understood that the methods and systems are not limited to specific methods, specific components, or to particular implementations. It is also to be understood that the terminology used herein is for the purpose of describing particular aspects only and is not intended to be limiting.

As used in the specification and the appended claims, the singular forms "a," "an," and "the" also include plural elements unless the context clearly dictates otherwise. "Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of aspects of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. The present methods and systems may also take the form of web-implemented computer software. Any suitable computer-readable storage medium may be utilized including hard disks, CD-ROMs, optical storage devices, solid state memory devices, magnetic storage devices, etc.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Figure 6:
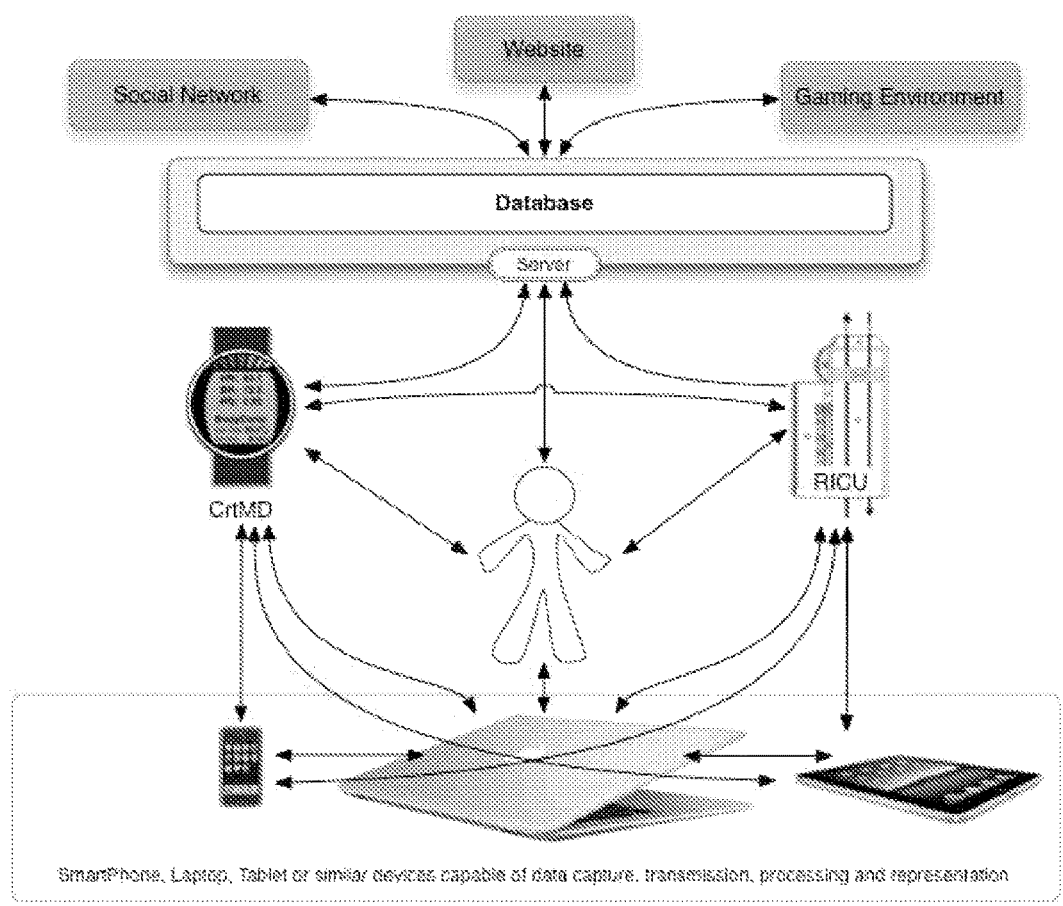
FIG. 6 is an example of how the Personalized Nutritional & Wellness Assistant manifests itself from the interaction of the various components of this patent, which includes (but is not limited to) the RICU, CrtMD, smartphone and similar devices, server-based website, social network and gaming environment.
Figure 7A:
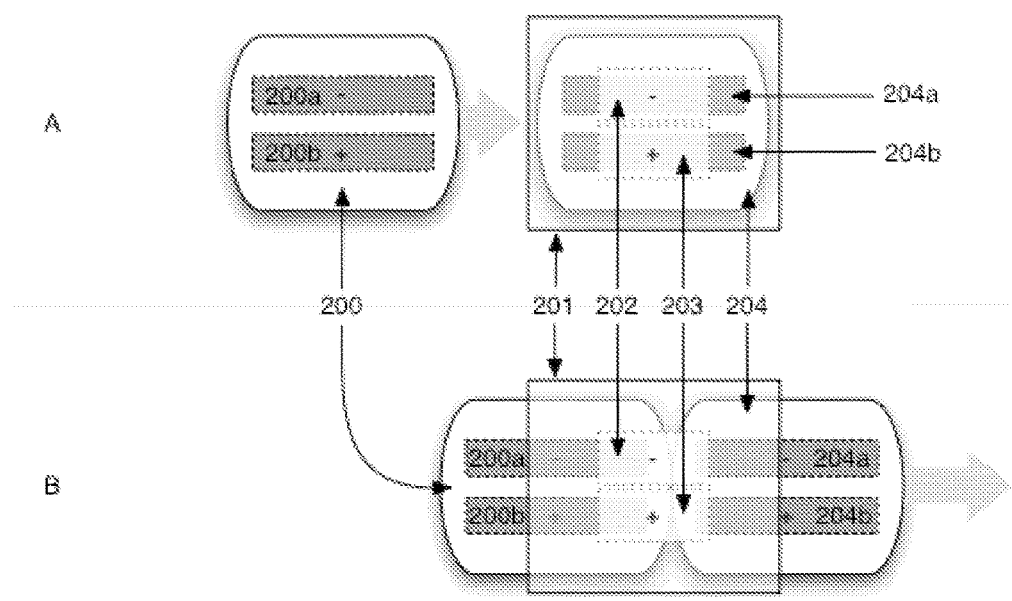
FIG. 7a is a schematic representation of one embodiment of a dual battery system used to provide an uninterrupted power supply to the electronic components of any electronic device when the battery/electrochemical cell has to be replaced.
Figure 7B:
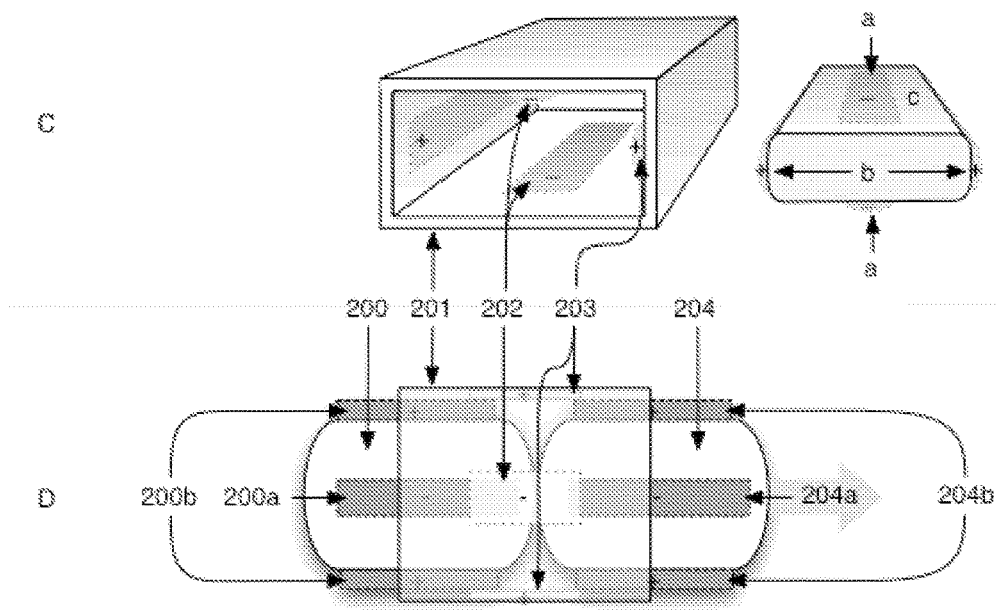
FIG. 7b is a schematic representation of one embodiment of the dual battery system, where circuit connectors are positioned on opposite sides of the battery and on opposite sides of the battery socket, to ensure complete non-directionality for insertion into the battery socket.

One embodiment of the present invention uses a Continuous Real-time Measuring Device (CrtMD) FIG. 1 powered by a Dual Battery System FIGS. 7a and 7b, where the CrtMD FIG. 1 is calibrated by a Regular Interval Calibration Unit (RICU) (depicted in FIGS. 2a and 2b and 2c and 9). Both the CrtMD and the RICU may be used to obtain physiological data about the user, and are capable of wireless and/or wired communication with other electronic devices (e.g. smartphones, tablets, PC's, web servers, each other, etc.) as shown in FIG. 3, FIG. 4, FIG. 5, FIG. 8 in order to update the Personalized Nutritional & Wellness Assistant of FIG. 6.

Continuous Real-time Measuring Device (CrtMD)

1. FIG. 1 depicts an exemplary embodiment of the CrtMD, in which the unit can be strapped to, for example, the user's arm (not shown) by means of a band 1, and the measured and/or calculated metabolic data are relayed for display and/or processing on the device itself, or on one or more external electronic devices (e.g. smartphones, tablets, personal computers, laptops and/or servers, etc.) by means of a wired or wireless transmitter 4. The device may be strapped to any part of an individual's body (including but not limited to the upper arm, lower arm, leg and torso with preferred positioning in one embodiment on the lower arm) which allows the light emitting module 8 and light detecting module 9 to be in close enough proximity to the user's skin surface to allow for continuous and accurate measurement of physiological parameters. In one embodiment of the invention, the CrtMD includes a GPS 3, an accelerometer (not shown), a clock (not shown), and utilizes an array of LEDs 8 producing light in the visible and/or near-infrared (NIR) spectrum (e.g. a light spectra ranging but not limited to the range 300 nm to 1100 nm) to illuminate the skin at frequent intervals. The emitted light may be diffused by the user's skin and underlying tissue (not shown) and the reflected light is detected by a light detecting module 9, consisting of a single photodiode, photodiode array or other sensors used for photo detection. Photodiode detection patterns may be amplified by an operational amplifier 9q, and may be digitized by means of one or more processing modules 7. Digitized signals may be used to resolve physiological parameters such as (but not limited to) heart rate, breathing rate, hemoglobin concentration, carbaminohemoglobin concentration, oxyhemoglobin concentration, oxygen saturation, etc. In one embodiment, the method is envisaged to involve:
    1. Interpolation of continuous wavelength spectra in a desired wavelength region (such as, but not limited to, 300-1100 nm) from the spectral data received from the respective photodiodes mounted on the photodiode array 9.
    2. Pre-processing of the obtained spectral data to increase the signal-to-noise (S/N) ratio. The preferred method can be a low pass filter method such as the Savitsky-Golay filter, but other methods such as multiple spectra averaging or mean-centering can be used to increase the S/N ratio.
    3. Using several regression algorithms to construct a mathematical model that can use x-y data (where x is optical wavelengths or frequencies and y is reflective or absorptive intensities corresponding to these wavelengths or frequencies) to predict a physiological parameter from the pre-processed data. In practice, one may obtain spectral data along with measured physiological parameters at different physiological conditions (e.g. during rest or during different levels of physical exertion) and use a regression algorithm such as Multiple linear regression, principal component analysis (PCA), non-linear iterative partial least squares (NIPALS) and/or partial least squares (PLS) regression to construct a mathematical model to predict the physiological parameter at hand.
    4. Validating the mathematical model constructed for each physiological parameter to see whether it has predictive ability for a validation data set (obtained at different physiological conditions, such as during rest and during different levels of physical exertion). In one embodiment, it is advisable that the constructed mathematical model yield an $R^2$ value greater than 0.96 ($R^2 > 0.96$).
    5. Saving the mathematical models to the online server and/or on the local storage module 101 of the CrtMD, to ensure rapid conversion of all subsequent raw photodiode signals to physiologically relevant data.

In one embodiment, this method may be performed once only, and can be used without prior knowledge of the molecular mechanism underlying the physiological parameter's quantification by spectrometry. This provides a unique advantage over other methods of spectral data resolution currently in use (near-infrared determination of oxyhemoglobin ($HbO_2$) concentration, for instance, relies on the spectral signature of the oxygenated heme-groups contained within the hemoglobin protein complex. It is therefore known that $HbO_2$ concentrations can be determined by considering 660 nm and 940 nm spectra, as the spectral differences for different $HbO_2$ concentrations are most pronounced at these wavelengths). By overcoming the requirement for prior knowledge of such underlying molecular mechanisms, the method of the current invention has the capacity to 'discover' physiological parameters of interest from the unresolved spectral signal and, as such is more versatile than current methodologies in its capacity to resolve physiological parameters from spectral data.

The CrtMD is able to deduce mood, sleep and stress states of a user by monitoring the cardiorespiratory system (and possibly adjusting the conclusions drawn from the measured data with mood/stress/sleep information that is manually provided by the user). This is possible because both the mood and the circadian rhythm (i.e. sleep/wake cycle) of human beings are reflected in their real-time metabolic and cardiorespiratory data. Sleep, for instance, is indicated by a reduction in cardiorespiratory activity (i.e. a reduction in respiratory frequency and pulse rate), while mood and stress levels are indicated by changes in photoplethysmographic data (e.g. changes in heart rate variability).

One feature of the CrtMD is its ability to distill the user's instantaneous oxygen consumption rate ($VO_2$) and instantaneous carbon dioxide production rate ($VCO_2$) from the resolved spectral data. This ability provides the CrtMD with the capacity to continuously calculate the real-time respiratory quotient (rtRQ) of the user, which in its turn is used to determine the real-time energy uptake of the user.

The following is a detailed description of the mathematical logic used for the distillation of the instantaneous oxygen consumption rate ($VO_2$) and instantaneous carbon dioxide production rate ($VCO_2$) from the resolved real-time spectral data, according to one embodiment of the present invention. The procedure involves manually specified parameters (e.g.

age), as well as initial calibration of the CrtMD (refer to Calibration of the CrtMD using the RICU, described further below) to obtain the resting physiological parameters necessary for substitution into functions 36a-36x (functions 36a-36x being representative of the mathematical logic underlying functions 35 and 36):

1. The user's $VO_{2max}$ is determined from the ratio of the user's maximum heart rate ($HR_{max}$) and resting heart rate ($HR_{rest}$) using the method of Uth et al. This requires expression of the user's $VO_2$ in terms of the cardiac output (Q) and the arterio-venous $O_2$ difference ($C_aO_2-C_vO_2$), using the Fick principle:

$$\dot{V}O_2 = \dot{Q} \cdot (C_aO_2 - C\bar{v}O_2) \quad [36a]$$

where cardiac output (Q)=heart rate (HR)×stroke volume (SV), such that:

$$\dot{V}O_2 = HR \cdot SV \cdot (C_aO_2 - C\bar{v}O_2) \quad [36b]$$

and the formula is true for a user at rest:

$$\dot{V}O_{2rest} = HR_{rest} \cdot SV_{rest} \cdot (C_aO_2 - C\bar{v}O_2)_{rest} \quad [36c]$$

or at maximal exertion:

$$\dot{V}O_{2max} = HR_{max} \cdot SV_{max} \cdot (C_aO_2 - C\bar{v}O_2)_{max} \quad [36d]$$

Combining the above equations, we get:

$$\dot{V}O_{2max} = \frac{HR_{max} \cdot SV_{max} \cdot (C_aO_2 - C\bar{v}O_2)_{max}}{HR_{rest} \cdot SV_{rest} \cdot (C_aO_2 - C\bar{v}O_2)_{rest}} \cdot \dot{V}O_{2rest} \quad [36e]$$

According to Nottin et al. (2002) the average value for $SV_{max}/SV_{rest}$ is 1.28 and in an independent study, Chapman et al. (1960) reported the average $SV_{max}/SV_{rest}$ value to be 1.29. By substituting the average of these two values (1.285) along with the average ratio of the arterio-venous oxygen difference at maximal oxygen consumption and at rest (3.4, as determined by Chapman et al. (1960)) into the equation, we get a reduced equation:

$$\dot{V}O_{2max} = 4.37 \frac{HR_{max}}{HR_{rest}} \cdot \dot{V}O_{2rest} \quad [36f]$$

2. The reduced equation is combined with a function relating 'HR proportional to $HR_{max}$' ($HR/HR_{max}$) to '$VO_2$ proportional to $VO_{2max}$' ($VO_2/VO_{2max}$):

$$\frac{\dot{V}O_2}{\dot{V}O_{2max}} = f\left(\frac{HR}{HR_{max}}\right) \quad [36g]$$

to obtain a complex equation:

$$\dot{V}O_2 = 4.37 \cdot \dot{V}O_{2rest} \cdot \frac{220 - \text{age}}{HR_{rest}} \cdot \left(f\left(\frac{HR}{HR_{max}}\right)\right) \quad [36h]$$

where $HR_{max}$ can be replaced with 220—age (as $HR_{max}$ can be approximated by using the formula 220—age).

3. The function is generalized to a form (e.g. a second order polynomial, or other regression equations) where several additional resting and real-time physiological parameters can be considered. An example of such a function would be:

$$\dot{V}O_2 = \quad [36i]$$
$$4.37 \cdot \dot{V}O_{2rest} \cdot \frac{220 - \text{age}}{HR_{rest}} \cdot \left(a \cdot \left(\frac{HR}{220 - \text{age}}\right)^2 - b \cdot \frac{HR}{220 - \text{age}} + c\right)$$

where a, b and c are functions of resting and/or real-time values for parameters such as (but not limited to) tissue hydrogen ion concentration (pH), hemoglobin concentration (Hb), breathing rate (BR), oxygen saturation ($SaO_2$), and oxyhemoglobin concentration ($HbO_2$). These functions can be formally written as:

$$a = \zeta_1((pH, Hb, BR, SO_2, HbO_2)_{rest}, (pH, Hb, BR, SO_2, HbO_2)_{RT}) \quad [36j]$$

$$b = \zeta_2((pH, Hb, BR, SO_2, HbO_2)_{rest}, (pH, Hb, BR, SO_2, HbO_2)_{RT}) \quad [36k]$$

$$c = \zeta_3((pH, Hb, BR, SO_2, HbO_2)_{rest}, (pH, Hb, BR, SO_2, HbO_2)_{RT}) \quad [36l]$$

where the functions $f_1$, $f_2$ and $f_3$ are determined by a parameter estimation approach (e.g. using neural networks).

4. The user's $VCO_2$ may be obtained in a similar manner as described for $VO_2$. The user's resting $VCO_2$ is first expressed in terms of the cardiac output (Q) and the arterio-venous $CO_2$ difference ($C_aCO_2-C_vCO_2$):

$$\dot{V}CO_{2rest} = HR_{rest} \cdot SV_{rest} \cdot (C_aCO_2 - C\bar{v}CO_2)_{rest} \quad [36m]$$

where heart rate ($HR_{rest}$)×stroke volume ($SV_{rest}$) replaces cardiac output (Q) in the original formula. Similarly, the user's $VCO_2$ at maximal exertion is expressed as:

$$\dot{V}CO_{2max} = HR_{max} \cdot SV_{max} \cdot (C_aCO_2 - C\bar{v}CO_2)_{max} \quad [36n]$$

and the two formulas are combined to give:

$$\dot{V}CO_{2max} = \frac{HR_{max} \cdot SV_{max} \cdot (C_aCO_2 - C\bar{v}CO_2)_{max}}{HR_{rest} \cdot SV_{rest} \cdot (C_aCO_2 - C\bar{v}CO_2)_{rest}} \cdot \dot{V}CO_{2rest} \quad [36o]$$

Although the $SV_{max}/SV_{rest}$ ratio can be replaced by 1.285 as before, the ratio of the arterio-venous carbon dioxide difference at maximal exertion and at rest is not known. The missing value is calculated from the arterio-venous oxygen difference at rest and maximal exertion, and the respiratory quotient at rest and maximal exertion, using the following procedure:

a. The user's resting respiratory quotient ($RQ_{rest}$) is written in terms of his/her arterio-venous oxygen and arterio-venous carbon dioxide differences at rest:

$$(C_aCO_2 - C\bar{v}CO_2)_{rest} = RQ_{rest}(C_aO_2 - C\bar{v}O_2)_{rest} \quad [36p]$$

which could also be written as:

$$(C_aCO_2 - C\bar{v}CO_2)_{rest} = RER_{rest}(C_aO_2 - C\bar{v}O_2)_{rest} \quad [36q]$$

because the respiratory quotient (RQ, representing gas exchange at the cellular level) is equal to the respiratory exchange ratio (RER, representing gas exchange in the lungs) when measured at rest.

b. Similarly, the user's respiratory quotient at maximal exertion ($RQ_{max}$) is written in terms of his/her arterio-venous oxygen and arterio-venous carbon dioxide differences at maximal exertion:

$$(C_aCO_2 - C\bar{v}CO_2)_{max} = RQ_{max}(C_aO_2 - C\bar{v}O_2)_{max} \quad [36r]$$

which could also be written as:

$$(C_aCO_2 - C\bar{v}CO_2)_{max} = (C_aO_2 - C\bar{v}O_2)_{max} \quad [36s]$$

because the cellular respiratory quotient at maximal expenditure equals one (i.e. $RQ_{max}=1$). In this case, use of the maximal respiratory quotient ($RQ_{max}$) is preferred over substitution with the maximal respiratory exchange ratio ($RER_{max}$), because the latter is influenced by metabolic acidosis and other $CO_2$ liberating processes that occur when the user's metabolic rate increases. These processes allow RER-values to vary from 0.7 to more than 1.2, while RQ-values remain in the range of 0.7 to 1.0.

c. The modified equations are substituted into equation 36o to obtain a complex equation:

$$\dot{V}CO_{2max} = \frac{HR_{max} \cdot SV_{max} \cdot (C_aO_2 - C\bar{v}O_2)_{max}}{HR_{rest} \cdot SV_{rest} \cdot RER_{rest} \cdot (C_aO_2 - C\bar{v}O_2)_{rest}} \cdot \dot{V}CO_{2rest} \quad [36t]$$

which can be reduced to:

$$\dot{V}CO_{2max} = 4.37 \frac{HR_{max}}{HR_{rest} \cdot RER_{rest}} \cdot \dot{V}CO_{2rest} \quad [36u]$$

by substituting the literature values for $SV_{max} \times SV_{rest}^{-1}$ (1.285) and the average ratio of the arterio-venous oxygen difference at maximal oxygen consumption and at rest (3.4) into the equation.

It should be noted that the $VCO_{2max}$ value obtained by this procedure is representative of respiration at the cellular level only. It should also be noted that $VCO_2$ values exceeding the $VCO_{2max}$ value are representative of cellular respiration as well as non-metabolic $CO_2$ liberation from the hemoglobin molecules as a result of metabolic acidosis and other $CO_2$ liberating processes.

5. A polynomial function is then developed, using a method similar to the one described in Saalasti (2003). The function describes the relationship between pHR and '$VCO_2$ proportional to $VCO_{2max}$' (pVO2):

$$\frac{VCO_2}{VCO_{2max}} = \sum_{i=0}^{n} a_i \cdot \left(\frac{HR}{HR_{max}}\right)^i \quad [36v]$$

where n is the order of the polynomial.

6. Combining equations 36u and 36v, and substituting $HR_{max}$ with 220—age, we get:

$$VCO_2 = 4.37 \cdot \frac{220 - age}{HR_{rest} \cdot RER_{rest}} \cdot VCO_{2rest} \cdot \sum_{i=0}^{n} a_i \cdot \left(\frac{HR}{HR_{max}}\right)^i \quad [36w]$$

where $a_i$ is a function of resting and real time values for tissue pH (pH), hemoglobin concentration (Hb), breathing rate (BR), tissue oxygen saturation ($SaO_2$) and oxyhemoglobin concentration ($HbO_2$), and is formally written as:

$$a_i = \zeta_i((pH, Hb, BR, SO_2, HbO_2)_{rest}, (pH, Hb, BR, SO_2, HbO_2)_{RT}) \quad [36x]$$

where $1 \leq i \leq n$, and the function $f_i$ is determined by a parameter estimation approach (e.g. neural networks or genetic algorithms).

Figure 3:
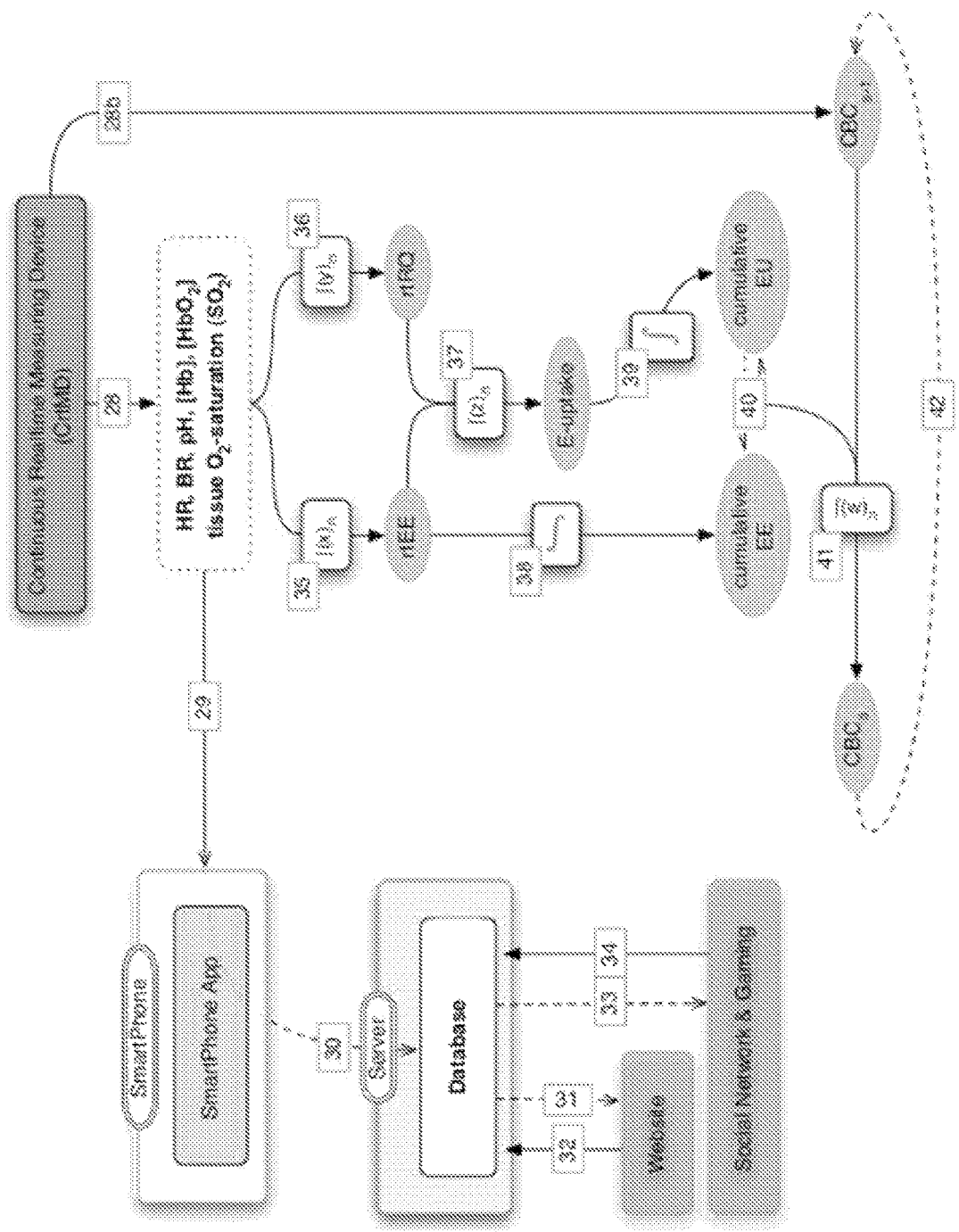
FIG. 3 is a schematic representation of one embodiment of a flow of information with regards to (a) device communication and (b) the calculations used to transform measured values into useful metabolic parameter output on the "Continuous Real-time Monitoring Device" (CrtMD).

FIG. 3 provides an illustration of how metabolic parameters such as the real-time respiratory quotient (rtRQ) 35, real-time energy expenditure (rtEE) 36, energy uptake (EU) 37, cumulative energy expenditure (cumulative EE) 38, cumulative energy uptake (cumulative EU) 39 and supposed current body composition ($CBC_s$) 40 can be calculated from the resolved physiological parameter data and distilled $VO_2$ and $VCO_2$ values of the user. It will be appreciated that the current invention is not limited to these calculations, however, and that other calculations with relevance to the user's metabolism, health and wellbeing are included in the present patent specification. Examples of such functions include those for calculation of the:

a. Real-time respiratory quotient (using real-time $VO_2$- and $VCO_2$-values):

$$rtRQ = \frac{VCO_2}{VO_2}$$

b. Total energy expenditure (substituting the real-time $VO_2$- and $VCO_2$-values into the Abbreviated Weir Formula):

$$TEE = 1.44 \cdot (3.9 \cdot VO_2 + 1.1 \cdot VCO_2)$$

c. Resting energy expenditure (substituting $VO_{2rest}$ and $VCO_{2rest}$ into the Abbreviated Weir Formula):

$$REE = 1.44 \cdot (3.9 \cdot VO_{2rest} + 1.1 \cdot VCO_{2rest})$$

d. Physical activity energy expenditure:

$$PAEE = TEE - REE$$

In one embodiment, all of the functions used are stored on a server, while all raw and/or resolved and/or locally calculated parameter data are stored on the local storage module 101. All values are time-stamped, and in one embodiment the most recently calculated supposed current body composition value ($CBC_s$) always replaces the previously saved supposed current body composition value ($CBC_{s-1}$) on the storage module 101. The data on the local storage module 101 can be directly transmitted to a server by means of a wireless transmitter 4 or a non-wireless communication port (not shown), or in step-wise fashion through the use of a smartphone or similar relaying device. A rechargeable battery and/or energy-harvesting device 6 serves as a power source for all of the energy dependent components of the CrtMD.

In one embodiment of the invention, the calculated metabolic parameters may be displayed on a smartphone application, tablet application, website, or the like, along with the resolved physiological parameter data of interest (e.g. heart rate, breathing rate, hemoglobin oxygen saturation, whole blood pH). In another embodiment of the invention, the resolved physiological data can be relayed to the user by means of a digital display (not shown), which also could be used as an interface to the user's social networks and/or web based, local and/or social network gaming environments. The user's progress with regards to his/her personal goal (refer to description of "Nutritional & Wellness Assistant") can also be indicated by progressive illumination of a colored light array (not shown).

Other embodiments of the CrtMD include: Incorporating the electronics of the CrtMD into a patch like form factor (i.e. a reusable or disposable patch that can be directly stuck onto the user's body) or into textiles or other materials that have direct contact with the body (e.g. normal clothing such as a sweater, shorts or shoes); allowance for different wavelengths to be measured in series by powering a set of LEDs sequentially; multi-step transmission of data to and from the server (e.g. the wearable device could transmit raw or resolved spectral data to a mobile phone, smartwatch (e.g. Pebble/i'm Watch), or any similar device using a wireless/wired communication protocol 26, from where it can be transmitted to an online server using GPRS/EDGE/3G/4G or any other wireless/wired modalities 27; data processing and/or display can occur either on the wearable CrtMD device or on the intermediary device (such as a mobile phone) or on the server; allowance for wireless/wired transference of data between hardware components, as well as data display by any of the components; allowance for audible communication of information to the user; allowance for verbal communication of queries and commands from the user to the device, etc.

CrtMD Data Processing

In one embodiment, the light detecting module 9 on the CrtMD generates a voltage or current proportional to the intensity of the light signal detected by the module 9. The level and amplitude of this signal is fed as parameters to a mathematical function which calculates the values that a PGA (programmable gain amp) has to be set at to create the specific level and gain adjustment necessary to amplify the detected light signal in order to make optimal use of the range of voltages sampled by a microcontroller or ADC (Analog to Digital Controller). The procedure is performed once, periodically or continuously to ensure that the signal remains in the microcontroller or analog-to-digital converter (ADC) sampling range. The signals measured by the microcontroller can be converted back to the original voltage or current as measured by the light-sensing module by reversing the calculation operations and taking into consideration the specific subtraction and gain adjustment. The original voltage or current can then be standardized by considering the sensing capability of the light detecting module 9, the distance of the light source from the light detecting module 9, as well as the luminosity of the light source generating the light measured by the light detecting module 9. This standardization enables one to compare the signal obtained by the light detecting module 9 when different intensities, position of luminosity and wavelengths of light are shone in the vicinity of the light detecting module 9.

Dual Battery System

FIG. 7a and FIG. 7b represent two embodiments of a dual battery system which may be used to provide an uninterrupted power supply to the electronic components of the CrtMD (or any other electronic device not covered by this patent) when a battery/electrochemical cell has to be replaced. The system may comprise a battery socket 201 with the positive contact point(s) 203 and the negative contact point(s) 202 positioned in such a way that a depleted battery 204 can be replaced by a charged battery 200 without interruption of the electrochemical circuit. In one embodiment of the invention, the charged battery 200 is used to push the depleted battery 204 out of the battery socket 201 as depicted in FIG. 7a (A and B) and FIG. 7b (C). In the embodiment of FIG. 7b (C), the battery socket 201 contains positive contact points 203 on opposite sides of the socket walls, and/or negative contact points 202 on opposite sides of the socket walls. The battery itself (c) could have one or more positive terminals (200b or 204b) and one or more negative terminals (200a or 204a), provided that these are positioned in such a way that they ensure contact with at least one negative contact point 202 and at least one positive contact point 203 inside the battery socket 201 before causing the depleted battery to break circuit when pushing it out of the battery socket 201. In another embodiment of the invention, the battery socket contains only one positive contact point 203, and one negative contact point 202, while the battery/electrochemical cells designed for use with the socket contains at least two positive terminals (200b or 204b) and at least two negative terminals (200a or 204a) positioned such that they ensure contact with at least one negative contact point 202 and at least one positive contact point 203 inside the battery socket 201 before causing the depleted battery to break circuit when pushing it out of the battery socket 201 with a charged substitute 200. In yet another embodiment of the invention, the socket may contain only three contact points (i.e. (i) 2 positives 203 and one negative 202, or (ii) 1 positive 203 and two negatives 202), while the battery/electrochemical cell itself contains the complementary set of terminals (i.e. (i) 1 positive (200b or 204b) and two negatives (200a or 204a), or (ii) 2 positives (200b or 204b) and one negative (200a or 204a)). Similarly, these terminals and contact points may be positioned such that they ensure an uninterrupted circuit when replacing a depleted battery/electrochemical cell 204 with a charged substitute 200.

Regular Interval Calibration Unit (RICU)

The Regular Interval Calibration Unit (RICU) comprises a portable and hand-held indirect calorimetric device with the capacity to obtain the metabolic parameters of a subject (i.e. a human, animal, plant or any other organism or process involving respiration or combustion). The RICU can determine important physiological parameters such as the carbon dioxide production rate ($CO_2$prod) and the oxygen consumption rate ($O_2$cons) of the user by analyzing the composition of both inspired air and/or expired air in the sampling chamber 26. In the preferred embodiment FIG. 2b, exhaled air samples are passively diverted from the air flow path 11, into the sampling chamber 26, through a sampling portal 181. In another embodiment FIG. 2a, inhaled and/or exhaled air samples are periodically diverted from the air flow path 11, into the sampling chamber 26, through a sampling valve 18.

Figure 2A:
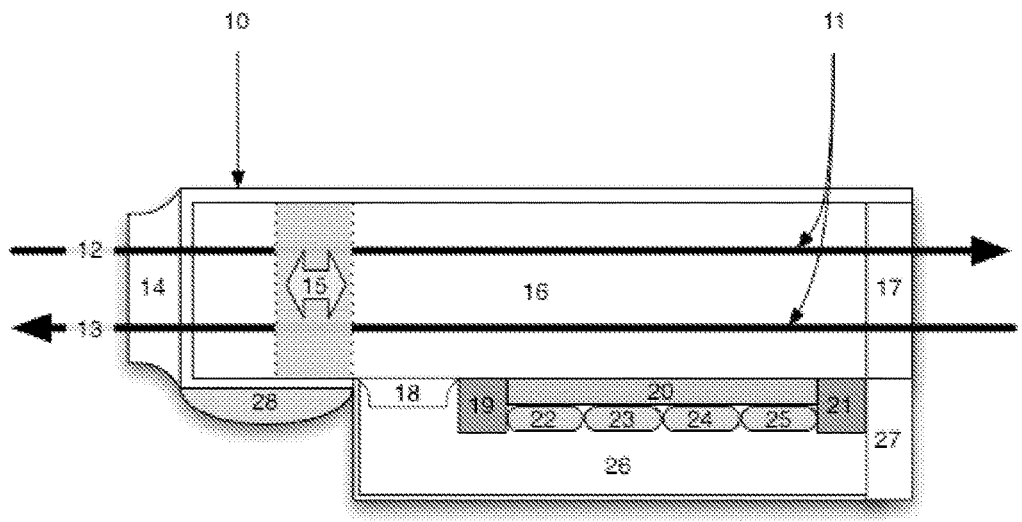
FIG. 2a is a schematic representation of an exemplary embodiment of the "Regular Interval Calibration Unit" (RICU) used for measuring physiological and/or metabolic parameters of a subject, and also used for regular interval calibration of the CrtMD—here depicted with a side stream analysis chamber.
Figure 2B:
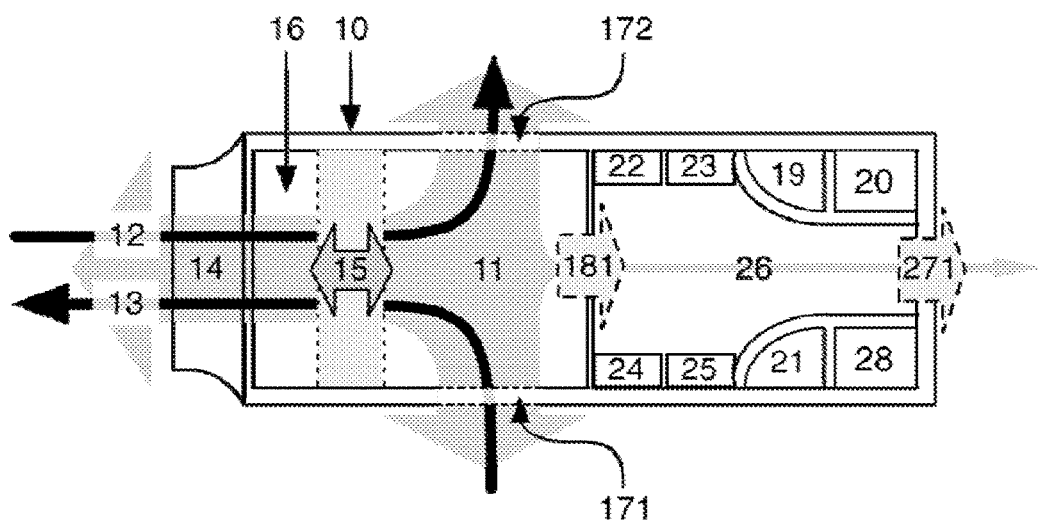
FIG. 2b is a schematic representation of one embodiment of the RICU—here depicted with a passive sampling analysis chamber.

FIG. 2b provides a schematic representation of one embodiment of the RICU, where the device includes a portable body 10 with a hollow interior 16 along which an airflow path 11 that runs between an inlet 171 (which could potentially simultaneously serve as an outlet), an outlet 172 (which could potentially simultaneously serve as an inlet, or be omitted altogether), a connector 14, and a passive sampling portal 181 which allows air to enter the sampling chamber 26 from which it can exit passively or actively (e.g. through forced ventilation by means of a fan or purge pump) through a purge portal 271. The connector 14 is attached to the portable body 10 in order to support contact of the subject's nose and/or mouth (not shown) to the device, and is designed to permit the complete volume of inhaled- and/or exhaled air to be passed into the device and along the air flow path 11 without loss due to leakage. The connector 14 may be detachable, or part of the device's body 10. Such connectors are well known and their design and functionality will not be further described here. A flow meter 15 is mounted across the air flow path 11 and is set to continuously measure the duration of inhalations ($MV_{inh}$, measured in volume per time unit) and/or exhalations ($MV_{exh}$, measured in volume per time unit), the duration of the breathing cycle, as well as the flow rate of the inhaled air flow 13 and/or the exhaled air flow 12. In one embodiment, each exhalation causes expired air 12 to passively enter the sampling chamber via the sampling portal 181. Passive sampling is achieved by means of (i) a non-return valve (not shown) positioned in the sampling portal 181 and/or purge portal 271; (ii) utilizing a valve that makes use of fluid dynamics rather than mechanical means (e.g. Gamboa, Bardell and Tesla valves) at the sampling portal 181 and/or purge portal 271; and/or (iii) designing the air flow conduit in such a way that it generates fluid dynamics that create a diodicity favoring net inflow of expired air into the sampling chamber 26.

FIG. 2a provides a schematic representation of an alternative embodiment of the Regular Interval Calibration Unit (RICU) where air samples are diverted from the main air flow stream by means of active sampling. The device includes a portable body 10 with an air flow conduit 16, along which an airflow path 11 that runs between a connector 14 and a vent hole 17. The device also includes a sampling chamber 26 into which air samples are directed by means of a sampling valve 18 in order to obtain air samples representative of the gas composition of inhaled air 13 and/or exhaled air 12. A connector 14 is attached to the portable body 10 in order to support contact of the subject's nose and/or mouth (not shown) to the device. As before, the connector 14 is designed to permit the complete volume of inhaled- and/or exhaled air to be passed into the device and along the air flow path 11 without loss due to leakage. Similarly, the connector 14 may be detachable, or part of the device's body 10. As in FIG. 2b, a flow meter 15 is mounted across the air flow path 11 and is set to continuously measure the duration of inhalations ($MV_{inh}$, measured in volume per time unit) and/or exhalations ($MV_{exh}$, measured in volume per time unit), the duration of the breathing cycle, as well as the flow rate of the inhaled air flow 13 and/or the exhaled air flow 12. In this embodiment, the sampling procedure could be performed in a single sampling event, or may be repeated several times during in- and/or exhalations to ensure that the samples are representative of the inspired and/or expired air. Signals from the sensors 22, 23, 24 and/or 25 can be used to determine when the breathing cycle has stabilized sufficiently to terminate the sampling procedure. The air sample can be released from the sampling chamber by opening the purge valve 27 by means of a mechanical- or electronic control mechanism (not shown).

Regardless of the sampling method, the sampling chamber is equipped with sensors capable of measuring the $O_2$ content 22, and/or $CO_2$ content 23, and/or temperature 24 and/or pressure 25 of the air inside. The $O_2$ and/or $CO_2$ sensors could be based on principles of electrochemistry (e.g. electrochemical cell); spectrophotometry (e.g. a non-dispersive infrared (NDIR) $CO_2$ sensor); colorimetry (e.g. the blue discoloration which occurs when $CO_2$ reacts with bromophenol blue); or any other method sensitive enough to provide accurate results. It will be appreciated that the current invention includes the use of any combined sensors that are able to measure any combination of the specified measured parameters. Also that the invention does not necessarily require the use of a flow meter 15, $O_2$ sensor 22, $CO_2$ sensor 23, thermometer 24 and pressure sensor 25, but could make use of only a select few of these to obtain data useful to calculate the unknown values. Similarly, some of the values may be assumed rather than measured—e.g. ambient pressure, temperature and/or humidity. In another embodiment of the invention, the accuracy of gas composition measurements is enhanced by reducing the amount of water vapor in air samples. In such an embodiment, the device includes water vapor scrubbers (not shown) positioned alongside or across the air flow path 11, inside the mouth piece 14, inside the sampling valve 18 or inside the sampling chamber 26. Temperature sensors (not shown) may also be positioned adjacent or inside the airflow path 11 to enable the measurement of local variations in temperature which could affect the accuracy of flow measurements.

FIG. 9 depicts the design of the air flow conduit and sampling portal of the RICU by means of which expired air 12 can be passively sampled into the sample analysis chamber 26 as a result of the fluid dynamics generated by the design. In this embodiment, the design of the air flow conduit 16 and sampling portal 181 create a diodicity favoring net inflow of expired air 12 into the sample analysis chamber 26, while air flowing through the air flow conduit as a result of an inhalation 13 will pass by the sampling portal 181 with only a negligible amount entering the sample analysis chamber 26. In the embodiment depicted here, the placement of the flow meter 15 and associated flow restrictor 900 further enhance the fluid dynamics generated by the design, thereby enhancing the diodicity that is created at the sampling portal 181 to favor net inflow of expired air 12 into the sample analysis chamber 26.

FIG. 9a depicts the comparative volumes of air passing through the connector 900, the first portal for allowing air into or out of the air flow conduit 171, the airflow conduit 16, the sampling portal 181, the purge portal 271, and the portal for allowing air into or out of the air flow conduit 172, where the thickness of the arrows represent the comparative volumes of air flowing through the system upon an exhalation 12.

FIG. 9b depicts the comparative volumes of air passing through the connector 900, the first portal for allowing air into or out of the air flow conduit 171, the airflow conduit 16, the sampling portal 181, the purge portal 271, and the portal for allowing air into or out of the air flow conduit 172, where the thickness of the arrows represent the comparative volumes of air flowing through the system upon an inhalation 13.

Although not essential for the passive sampling of expired gasses, the embodiment depicted in this figure further comprises a handheld body 10, a fan or pump for purging the sample analysis chamber 901, a power source 19 for powering the electronic components of the device (including those components useful for generating, receiving, transmitting or storing data 904), a sensor for measuring the ambient pressure 903 outside of the sample analysis chamber, and sensors capable of measuring the $O_2$ content 22, $CO_2$ content 23, temperature 24, humidity 25, or pressure 902 of the air inside the sample analysis chamber 26.

Figure 2C:
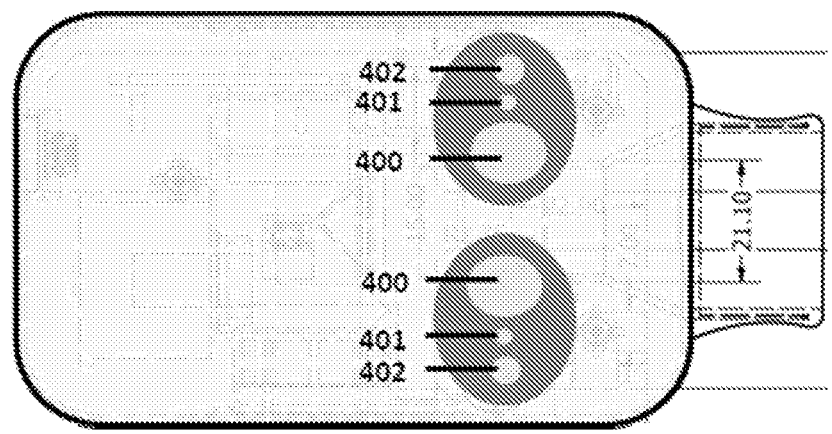
FIG. 2c is a schematic representation of one embodiment of the RICU—here depicted with sensors for bioelectrical impedance and heart rate monitoring.
Figure 2C:
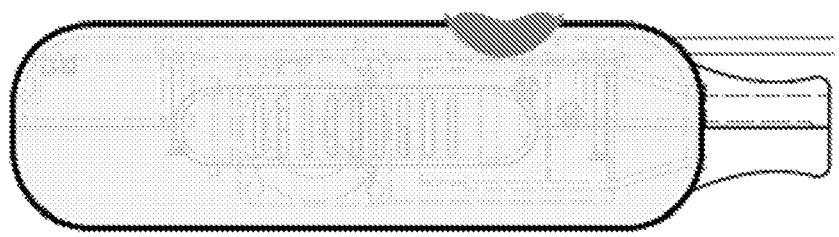
Figure 2C:
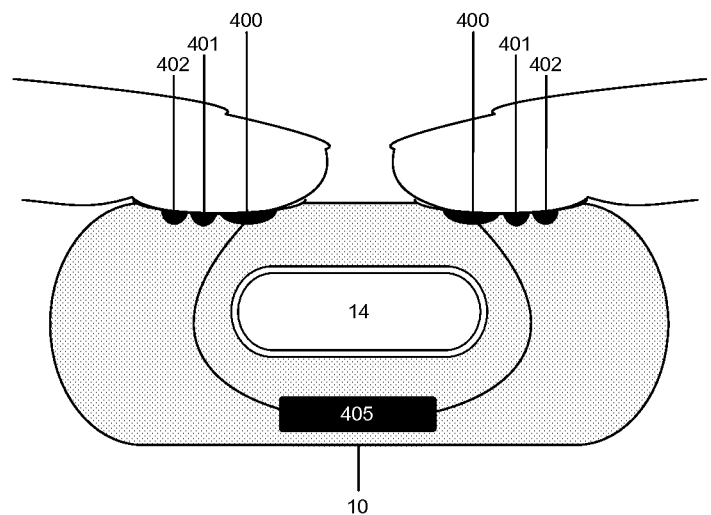

Regardless of the embodiment, all mechanical and electronic parts in the RICU may be powered by an internal and/or external power source 19. In one embodiment (regardless of the sampling method), the RICU includes a processing module 20 for processing the raw signals obtained from the flow meter 15, $O_2$ sensor 22, $CO_2$ sensor 23, thermometer 24 and pressure sensor 25. In such an embodiment, the processing module 20 may be able to calculate relevant metabolic parameters from the processed information, using a set of functions stored on the local storage unit 21, and raw signal data is stored on the local storage unit 21 along with all measured and calculated values. The data can be transmitted to a smartphone and/or server and/or similar device with suitable capabilities by means of a wireless transmitter 28 or a non-wireless communication port (not shown). As is illustrated in FIG. 2c, the RICU can also include surface electrodes 400 and phase sensitive electronics 405 for measurement of bioelectrical impedance, where the electrodes are positioned in such a way that a user has to place his/her finger(s) over them in order to use the device for breath analysis. In addition, the RICU could include light sources 402 and light detecting sensors 401 for measurement of heart rate, where these components 402 & 401 are likewise positioned such that a user has to place his/her finger(s) over them in order to use the device for breath analysis. In this embodiment, heart rate data is obtained by directing a light source 402 producing light in the visible and/or near-infrared (NIR) spectrum (e.g. a light spectra ranging but not limited to the range 300 nm to 1100 nm) onto the subject's skin. The emitted light is diffused by the user's skin and underlying tissues (not shown) and the reflected light is detected by a light detecting module 401, which could be a single photodiode, photodiode array or any other sensors used for photo detection. Photodiode detection patterns are amplified by an operational amplifier, and digitized by means of one or more processing modules. Digitized signals are used to resolve physiological parameters such as (but not limited to) heart rate and/or breathing rate.

Figure 4:
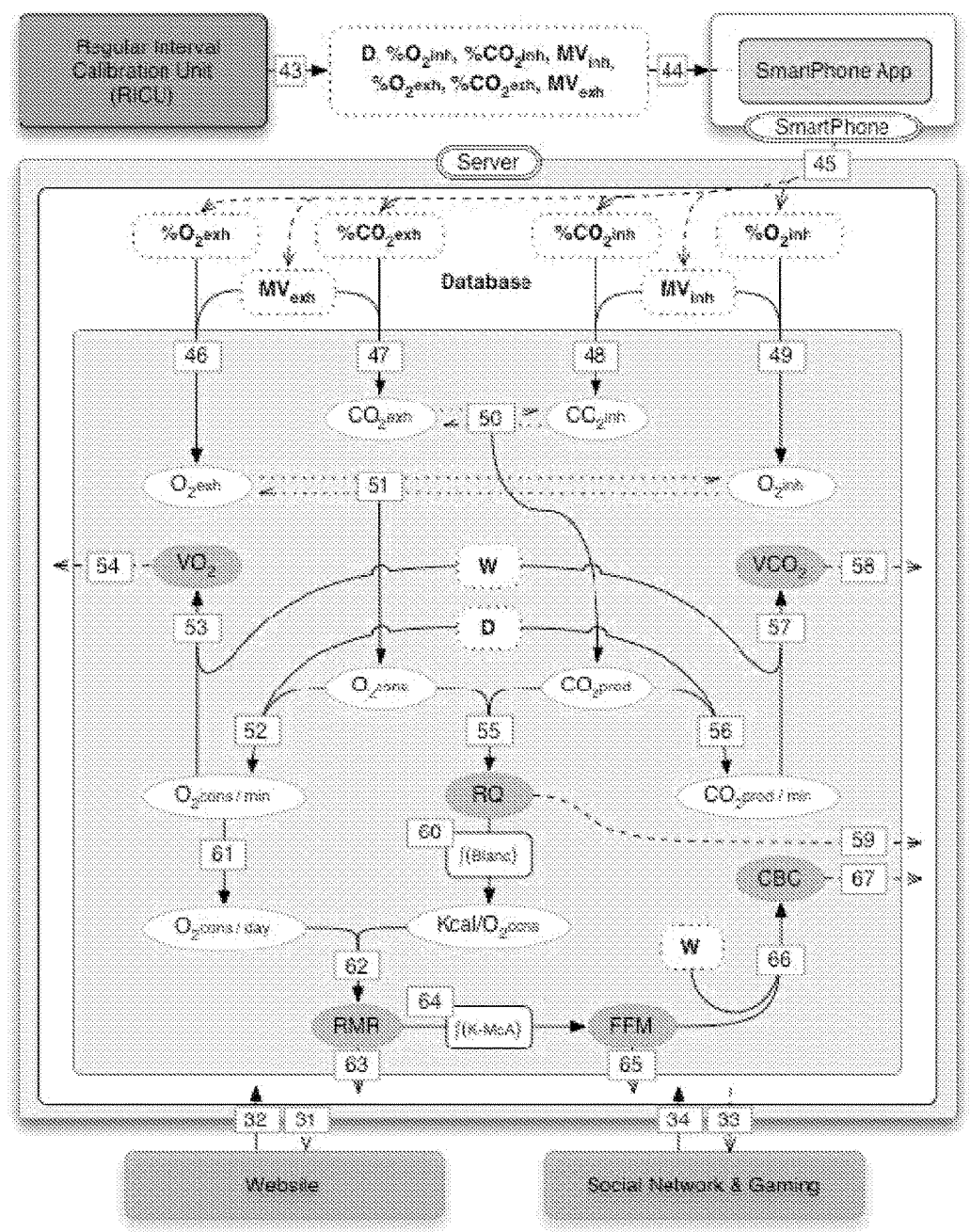
FIG. 4 is a schematic representation of one embodiment of a flow of information with regards to (a) device communication and (b) the calculations used to transform the values measured by the "Regular Interval Calibration Unit" (RICU) into useful metabolic parameter data that could be stored on the database.

FIG. 4 illustrates how the RICU processing module 20 and/or the server can utilize processed signals (i.e. MV, % $O_2$inh, % $CO_2$inh, % $O_2$exh and % $CO_2$exh) from the RICU sensors 15, 22, 23, 24, 25 to calculate the carbon dioxide production rate ($CO_2$prod) and oxygen consumption rate ($O_2$cons) using functions 46-51:

$$O_2\text{cons}=MV_{inh}\times\% \ O_2\text{inh}-MV_{exh}\times\% \ O_2\text{exh} \qquad [46],[49],[51]$$

$$CO_2\text{prod}=MV_{inh}\times\% \ CO_2\text{exh}-MV_{exh}\times\% \ CO_2\text{inh} \qquad [47],[48],[50]$$

The carbon dioxide production rate ($CO_2$prod) and oxygen consumption rate ($O_2$cons) measured by the current invention provides a very good approximation of the user's actual resting RQ, because the volume of the sampling chamber reflects the number of molecules in the sampling chamber when measured at standard temperature and pressure. The resting Respiratory Quotient (RQ) of the user is calculated from these values:

$$RQ=CO_2\text{prod}/O_2\text{cons} \qquad [55]$$

After which the amount of energy produced by the user (Q) can be calculated, using an equation from Blanc, S. et al. (1998):

$$Q=RQ\times 1.331+3.692 \qquad [60]$$

The Resting Metabolic Rate (RMR, in Kcal per day) can then be determined by multiplying the subject's energy production capacity (Q, in Kcal produced per liter of oxygen consumed by the user at rest) with the amount of oxygen consumed per day (S, measured in liters):

$$RMR=Q\times S \qquad [62]$$

And using the Katch-McArdle equation and the calculated Resting Metabolic Rate (RMR), it is then possible to determine the subject's fat free mass (FFM):

$$FFM=(RMR-370)/21.6 \qquad [64]$$

By combining the FFM with the user's weight, his/her/its body fat percentage can be determined:

$$\% \text{ Body Fat}=100\times(\text{WeightTotal}-FFM)/\text{WeightTotal} \qquad [66]$$

If measured at rest, and given that the user does not have an atypical metabolic profile, this value is analogous to the user's current body composition (CBC). As an optional internal control for the device, the user's parameters could be determined by means of bioelectrical impedance as well, and the values thus measured (e.g. % BodyFat, FFM and/or CBC) could also be used as input to the model.

Calibration of the CrtMD using the RICU

Figure 5:
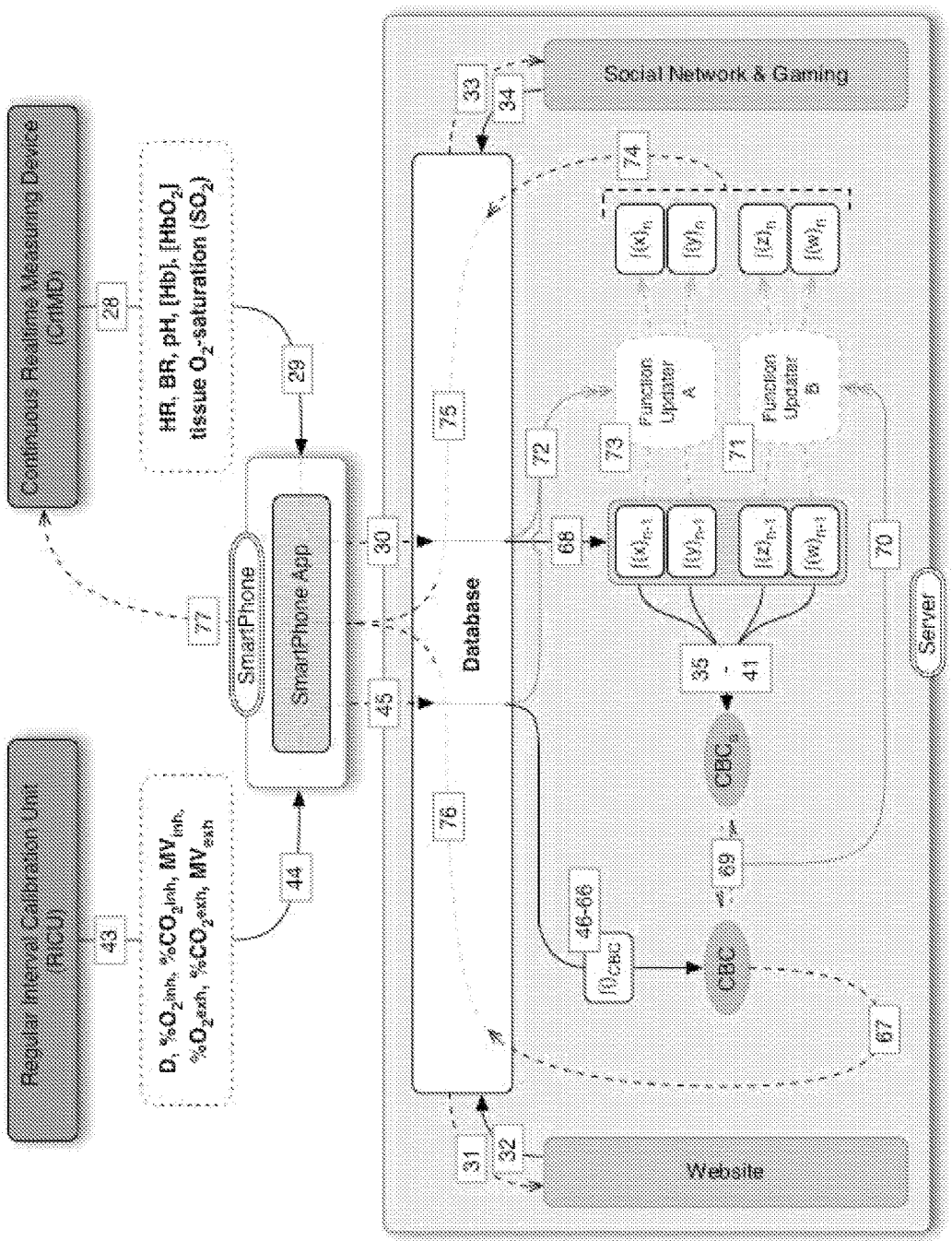
FIG. 5 is a schematic representation of one embodiment of the integration of information that underlies the calibration of functions used to calculate metabolic parameters on the server and CrtMD.
Figure 8:
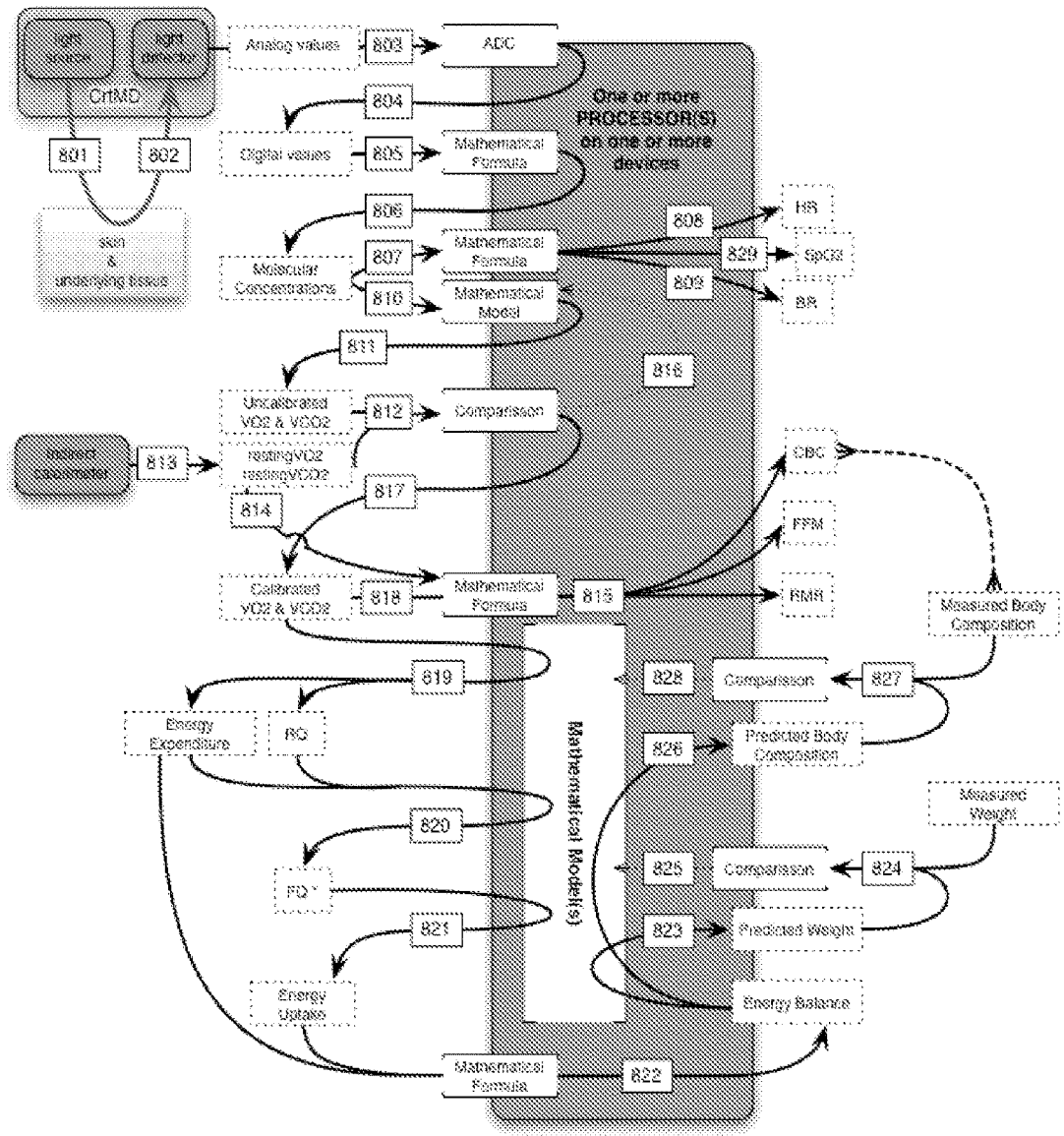
FIG. 8 depicts a process by which the CrtMD and RICU may operate, in one embodiment.

FIG. 5 and FIG. 8 depict the process by which the accuracy of the CrtMD may be increased through regular (e.g. weekly or monthly) calibration with the RICU, according to one embodiment. Calibration of the CrtMD is possible by using both devices at rest (i.e. in the morning just after waking up), and in one embodiment may require the transmission of all previously stored and recently measured data to the server to update its database (processes 28-30 and 43-45). The server will then utilize the most recent data obtained from the RICU (e.g. the directly measured resting $VO_2$ ($VO_{2rest}$) and resting $VCO_2$ ($VCO_{2rest}$) values) to calculate the user's resting respiratory quotient ($RQ_{rest}$) and actual current body composition (CBC), using functions 46-66. The server will also calculate the user's resting energy expenditure (REE) using the Abbreviated Weir Formula:

$$REE=1.44\cdot(3.9\cdot VO_{2rest}+1.1\cdot VCO_{2rest})$$

which an also be written in terms of $VO_{2rest}$ and $RQ_{rest}$ as:

$$REE=1.44\cdot(3.9\cdot VO_{2rest}+1.1\cdot(RQ_{rest}\cdot VO_{2rest}))$$

where $VO_{2rest}$=oxygen consumption (ml/min), $VCO_{2rest}$= carbon dioxide production (ml/min), $RQ_{rest}$=respiratory quotient=$VCO_{2rest}/VO_{2\_rest}$ and REE=resting energy expenditure (kcal/day). At the same time, the server will use the latest dataset obtained from the CrtMD to calculate the latest supposed current body composition ($CBC_s$), using functions $\zeta(x)_{n-1}$, $\zeta(y)_{n-1}$, $\zeta(z)_{n-1}$, and $\zeta(w)_{n-1}$ (corresponding to functions 35, 36, 37 and 41 stored on the local storage module 101 of the CrtMD). The first step of the calibration procedure occurs when the actual CBC-value (calculated from weight and RICU data) is compared 69 to the supposed CBC-value ($CBC_s$, calculated from the CrtMD sensor data) and the discrepancy is used to train a function updater 71 to optimize functions $\zeta(z)_{n-1}$, and $\zeta(w)_{n-1}$ for future calculations of $CBC_s$. In a parallel process, CrtMD and RICU data is combined 72 to train a second function updater to optimize functions $\zeta(x)_{n-1}$, and $\zeta(y)_{n-1}$ for future calculations of $CBC_s$. Process 74 illustrates how the improved functions $\zeta(x)$, $\zeta(y)$, $\zeta(z)$ and $\zeta(w)$ are used to update the server database, while processes 75 and 77 illustrates how outdated functions 35, 36, 37 and 41 (corresponding to functions $\zeta(x)_{n-1}$, $\zeta(y)_{n-1}$, $\zeta(z)_{n-1}$, and $f(w)_{n-1}$ on the server) on the Smartphone Application and/or the storage module 101 of the CrtMD can be updated if, in fact, these functions are stored on the devices themselves. Similarly, processes 67, 76 and 77 illustrate how the latest actual CBC-value is used to update the server database and replace the last stored supposed $CBC_s$-value ($CBC_{s-1}$) on the CrtMD storage module 101. Updated functions and values can be transmitted from the server to the devices via a wireless receiver 5 or a non-wireless communication port (not shown).

It will be appreciated that, although the RICU and CrtMD device suite has been designed to be complimentary, calibration of the CrtMD with any data similar to that provided by the RICU (e.g. $VO_2$, $VCO_2$, CBC, % BF, etc.) is also envisioned. Also, calibration of any other measuring device (e.g. Polar heart rate monitors, Garmin watches, Fitbit, BodyMedia Fit, etc.) by means of the data obtained from the RICU and/or CrtMD may also be performed.

It will also be appreciated that the RICU could be designed for single-user or multi-user purposes (in which case the device would include medical grade filters and removable mouth pieces).

FIG. 8 depicts a process by which the CrtMD and RICU may establish the various physiological and metabolic parameters of a subject's body (not shown); the process by which an indirect calorimeter (e.g. the RICU) may be used to calibrate the CrtMD; and the process by which direct measurement of various body parameters can be used to train the mathematical models that provide the information that the CrtMD or Personalized Nutritional and Wellness Assistant relays to the user.

In this figure, at least one light source is used to illuminate the subject's skin and underlying tissue 801, while at least one light detector receives the wavelengths reflected from the subject's skin and underlying tissue 802. The reflected wavelengths are converted to analog signals by the light detector, and may then serve as input 803 to an analog-to-digital-converter (ADC). The ADC may convert 804 the analog signals into digital values, which may subsequently be used as input 805 for one or more mathematical formulas by which the concentrations of various molecules (e.g. hemoglobin, carbaminohemoglobin, oxyhemoglobin, etc.) may be calculated 806. The calculated molecular concentrations may then serve as input 807 to yet more mathematical formulas by which physiological parameters such as heart rate (HR), breathing rate (BR) and oxygen saturation (SpO2) may be calculated 808, 809, 829. Alternatively, the calculated molecular concentrations may serve as input 810 into mathematical models by which the oxygen consumption rate ($VO_2$) and carbon dioxide production rate ($VCO_2$) of the subject may be resolved 811. In order to validate the accuracy of these mathematical model(s), the CrtMD may be used simultaneously with an indirect calorimeter (e.g. the RICU). The $VO_2$ and $VCO_2$ values measured by the CrtMD may then be compared 812 to the $VO_2$ and $VCO_2$ values measured 813 by the indirect calorimeter (e.g. the RICU). Whenever a discrepancy may occur between the calculated and the measured $VO_2$ and $VCO_2$ values, the measured $VO_2$ and $VCO_2$ values may be used to train 816 the mathematical models such that they become increasingly personalized (more accurate) over time—hence, the procedure described above is considered a calibration procedure for the CrtMD. The calibrated $VO_2$ and $VCO_2$ values obtained 817 from a calibrated CrtMD may subsequently serve as input 818 into at least one mathematical formula by means of which a number of metabolic parameters (e.g. the resting metabolic rate (RMR), the fat free mass (FFM) and the current body composition (CBC)) may be calculated. These parameters may also be calculated 814 from the $VO_2$ and $VCO_2$ values obtained 815 from an indirect calorimeter (such as the RICU) when used at rest. At the same time, the calibrated $VO_2$ and $VCO_2$ values may be used as input into at least one mathematical model by which the real-time respiratory quotient (RQ) and/or the energy expenditure (EE, i.e. calories burnt) may be calculated 819, while these values may in its turn serve as input into at least one mathematical model by which the food quotient (FQ) may be calculated 820. Similarly, energy uptake (EU, i.e. calories taken up into the body from the gut) may be calculated from FQ using at least one mathematical model 821. The calculated energy uptake and energy expenditure values may subsequently be used as input into a simple mathematical formula in order to calculate 822 the energy balance (EB) of the subject. The calculated energy balance value(s) may in its turn be used as input into at least one mathematical model by which the weight loss/gain of a subject may be predicted 823 for a defined time span. Similarly, the calculated energy balance value(s) may be used as input into at least one mathematical model by which the body composition of a subject may be predicted 826 for a defined time span.

Values obtained from other accurate and trustworthy measuring devices (e.g. another type of indirect calorimeter, body impedance measuring devices, a weighing scale, etc.) or food logging (where the quantity of food consumed and the macromolecular composition of the food consumed is provided) may be used to validate the accuracy of at least one of the mathematical models used to perform processes 819, 820, 821, 823 and 826. This may be done by comparing the calculated values (e.g. predicted weight, or predicted body composition) to the measured values (e.g. weight as measured by a weighing scale, or body composition as measured by a bio-electrical impedance measuring device). Whenever a discrepancy may occur between the calculated and the measured values, the measured values may be used to train 825, 828 at least one mathematical model in order for it to become more personalized (more accurate) over time. Note that, since the RICU can be used to calculate body composition for a subject at rest, this value may be used as a second calibration tier in the calibration procedure when simultaneously using the RICU and CrtMD at rest. Moreover, information such as age, gender, race, genetic markers, etc. may be introduced at any stage during the process in order to determine the values of at least one new parameter, or to make model parameterization more accurate (i.e. to train at least one mathematical model).

Personalized Nutritional & Wellness Assistant

An important aspect of the present invention is the supportive information system (henceforth called the 'Personalized Nutritional & Wellness Assistant') which complements the use of the CrtMD and RICU of the current invention. The Personalized Nutritional & Wellness Assistant represents all raw, measured and calculated data, as well as their transmission between any current or future electronic devices capable of data transformation and/or information display (e.g. the CrtMD, RICU, smartphones, tablets, personal computers, laptops, servers, etc.). The Personalized Nutritional & Wellness Assistant may also include manual input relevant to the metabolic assessment of the user (e.g. the height, weight and age of the user), as well as the personal health, wellness and/or sport performance goal(s) of the user.

The Personalized Nutritional & Wellness Assistant presents a novel and unique implementation of the field of Computational Systems Biology (a scientific field where multi-reaction biological systems and mathematical modeling are integrated), by utilizing the output of sensing devices (such as, but not limited to, the CrtMD and the RICU) as input variables and/or parameters into mathematical models designed to describe biological systems in silico. In one embodiment, the mathematical model(s) may comprise ordinary or partial differential equations, but the models can also be constructed with other discrete formulations, statistical formulations and stochastic formulations. Regardless of the method used, these mathematical models may use variables (i.e. model entities not staying constant—e.g. temperature; breathing rate; heart rate; enzyme rates; equilibrium driven reactions) and parameters (i.e. values describing the properties of the entities that are part of the model and that enable variables in the model to change over time). In a typical scenario, sensor data from a subject will be transmitted wirelessly (for instance via a smartphone), or non-wirelessly to a server (or any other device capable of computation) where it will serve as input variable(s) and/or parameter(s) to a computational platform of mathematical models and/or systems models that describe physiological and/or physical characteristics of that subject at enzyme level, tissue level, organ level, and/or whole body level. With the sensor data incorporated, these models may then generate output variables and/or parameters that can be stored on the server and/or transmitted from the server to a different location (i.e. the sensor device, a smartphone, tablet, other server etc.). In an alternative embodiment, sensor data will not be transmitted to remote computer systems, but will be analyzed locally on the processing module of the measuring device itself. One application of this method, for example, would be to use data obtained from the RICU and the CrtMD as input for variables and/or parameters to mathematical models of metabolism to predict and/or analyze several system variables and parameters such as, but not limited to, projected weight loss, projected body fat, projected energy uptake, Energy Balance, Excess Postexercise Oxygen Consumption, VO2, VCO2, Respiratory Exchange Ratio, Respiratory Quotient, Total Energy Expenditure, Resting Energy Expenditure, Physical Activity Energy Expenditure, etc.

The most basic function of the Personalized Nutritional & Wellness Assistant is to provide the user with a means to predict, track, calculate, analyze and display his/her wellness- and lifestyle related parameters in a number of ways and on a variety of devices. The Personalized Nutritional & Wellness Assistant is also able to assist the user in his/her decision making process with regards to a number of wellness related factors (e.g. whether or not to lose weight, how to improve fitness, deciding on a type of diet, knowing which exercise and sports programs will assist in attaining a personal health goal, etc.). In one embodiment, the Personalized Nutritional & Wellness Assistant is able to guide and motivate its user towards improved health, wellness and/or sport performance through the use of motivational feedback loops that are responsive to the user's continuously measured and calculated physiological and metabolic parameters. In such an embodiment, the efficiency of the motivational feedback loops may be improved on a continuous basis by altering the focus, frequency and type of motivators supplied to the user. A generalized description of a genetic algorithm approach suitable for such improvement would be as follows:

1. The user database is divided into subgroups (randomly, or according to user type), where each subgroup is of a sufficient size to perform statistical analysis.
2. Each subgroup is exposed to motivational feedback from the Personalized Nutritional & Wellness Assistant, but feedback differs with regards to type, timing, frequency, style and focus.
3. The efficiency by which each subgroup attains its various user-specified goals provides an indication of the effectiveness of the motivational messages sent to the users (i.e. the fitness function of the optimization algorithm, e.g. genetic algorithm or evolutionary strategy, uses consumer compliance, consumer satisfaction and consumer goal achievement as variables).
4. Subgroups displaying the greatest overall improvements are regarded as those that received the most effective motivational feedback from Personalized Nutritional & Wellness Assistant.
5. The type, timing, frequency, style and focus of motivational feedback provided to the top performing subgroups are paired and the offspring traits are assigned to all of the subgroups of the specific user type (or the complete user base). The cycle is repeated until all discernible differences between the performances of subgroups are minimized.
6. Statistical analysis (e.g. cluster analysis) can be used to identify user types that favorably respond to a general set of motivational prompt and data parameters.
7. New users can be assigned user types according to their personal profiles and therefore immediately benefit from the motivational prompt and data style (as well as other parameters) that is most likely to be beneficial to them.
8. The specific user's motivational prompt style can be fine-tuned or altered with further cycles of the above optimization algorithms.
9. Exclusion of tired and ineffective motivational strategies is ensured by continuously introducing new means of motivation (discovered from scientific literature, for instance) into the current motivational framework and allowing them to compete with the existing framework. The cycle can be continuous and can make use of artificial intelligence methods to perform an automated improvement cycle).

Body weight has a natural tendency to fluctuate because of fluid balance changes in an individual's body. This can cause abrupt measurable weight changes that do not reflect the actual change in body tissue weight of an individual as he/she progresses towards his/her goal. In order to prevent a user from losing motivation due to inconsequential weight fluctuations, the Personalized Nutritional & Wellness Assistant can employ a regular moving or rolling average to indicate the trend of weight change. The moving or rolling average acts as a general trend indicator and informs the user about his/her progress towards his/her goal by, for example, color coding the area between the moving average and weight input curve (the weight curve not averaged) when the user's weight fluctuates above or below the moving or rolling average trend line. In one embodiment of the invention, the area is colored red whenever the user makes negative progress with regards to his/her goal, and green whenever the user makes positive progress with regards to his/her goal. It will be appreciated, however, that the scope of the current invention is not limited to the use of red and green only, but could utilize any color scheme or visual cues deemed suitable to indicate positive and/or negative and/or neutral progress with regards to a user's goal.

As a result of the CrtMD's unique capacity to monitor the real-time respiratory quotient of the user, the Personalized Nutritional & Wellness Assistant has the capacity to provide the user with continuous real-time feedback about his/her current nutritional state (i.e. how much of which resource the user is utilizing for metabolic energy production at any given moment), energy uptake levels (i.e. amount of calories consumed within a given time frame), energy expenditure levels, and energy balance. Energy balance zones can be identified in accordance with the user's wellness goals, and the Personalized Nutritional & Wellness Assistant could be programmed to provide warning signals to a user whenever the user trespasses his/her personal energy balance boundaries, and/or motivational feedback to help the user stay within the specified boundaries. The Personalized Nutritional & Wellness Assistant can therefore also provide the user with instantaneous advice regarding the most suitable food sources to eat at any given time.

The Personalized Nutritional & Wellness Assistant is also able to discover and educate a user about patterns in his/her behavior that triggers unwanted and/or desirable physiological responses (e.g: A user might always feel 'tired' when he/she ate a carbohydrate dense meal the night before. This might not always be evident to the user, but the Personalized Nutritional & Wellness Assistant would be able to 'discover' these hidden patterns by continuously and/or intermittently considering all the system variables (i.e. user inputs, CrtMD data and RICU data)). By integrating the above mentioned 'discovery' capacity of the Personalized Nutritional & Wellness Assistant with geological data (e.g. GPS), behavioral data (i.e. online social interaction and purchase behavior), third party devices/services (e.g. Facebook™ or foursquare) and mood data, user feedback can be tailored to be more personalized and parameters of importance for other purposes (e.g. health risk analysis, sport performance and/or targeted advertising) could be identified.

In one embodiment, the Personalized Nutritional & Wellness Assistant is able to use the user's personal physiological and/or metabolic data to control an avatar in a web based, local and/or social network gaming environment. In a further preferred embodiment, the Personalized Nutritional & Wellness Assistant may be used to link to the user's social networks (e.g. Facebook™, Twitter, or any similar current and future networks) to enable social relations and interactions between users of any of the technologies described in the current invention.

Besides the above characteristics, the Personalized Nutritional & Wellness Assistant may also include a function store containing three categories of functionalities: (i) free functions, (ii) paid functions and (iii) subscription functions. As with Apple's appstore and Android's apps, devices may be issued with a default set of functions, while additional functions may downloaded from the function store. Third-party development of functions will encouraged by making the data obtained from the device suite accessible via an API.

The invention claimed is:

1. A system capable of transcutaneous measurement of a subject, wherein the system comprises:
   (a) at least one light source for shining light onto or through tissues of and under skin of the subject;
   (b) at least one light detector for receiving light reflected from the tissues of the subject's skin or from the tissues underlying the subject's skin and converting the reflected light into a detected signal; and
   (c) at least one component adapted to generate and store at least one value for each of $VCO_2$ and $VO_2$ from the detected signal, wherein $VO_2$ corresponds to an instantaneous rate of oxygen consumption of the subject and wherein $VCO_2$ corresponds to an instantaneous rate of carbon dioxide production by the subject, wherein the at least one component is further adapted to continuously calculate a real-time respiratory quotient of the subject from real-time values of $VCO_2$ and $VO_2$ and to use the real-time respiratory quotient to determine a real-time energy uptake of the subject.

2. The system of claim 1, wherein the at least one light source comprises a plurality of light sources that simultaneously or sequentially direct light of different wavelengths onto or through the tissues of and under the skin of the subject.

3. The system of claim 1, wherein the at least one light detector comprises a plurality of light detectors, each of which receives light of at least one wavelength.

4. The system of claim 1, wherein the system incorporates at least one operational amplifier or at least one microprocessor by means of which at least one digital potentiometer may be iteratively adjusted in order to obtain optimal amplification of the at least one detected signal.

5. The system of claim 1, wherein the at least one component stores, executes, transmits or receives a digital value, at least one mathematical function, at least one parameter of the at least one mathematical function, or any combination for generating at least one value of at least one parameter of physiology for the purpose of further mathematical calculation or for informing the subject of its physiological status.

6. The system of claim 5 wherein the at least one parameter of physiology may be selected from the group consisting of heart rate (HR), breathing rate (BR), hemoglobin concentration ($H_b$) oxyhemoglobin concentration ($H_bO_2$), carbaminohemoglobin concentration ($H_bCO_2$), oxygen saturation (SpO), oxygen consumption rate ($VO_2$), carbon dioxide production rate ($VCO_2$), Respiratory Exchange Ratio (RER), Food Quotient (FQ), Metabolic Fuel Composition (i.e. the macronutrient that a subject is utilizing as metabolic fuel at a given instance), Total Energy Expenditure (TEE), Resting Energy Expenditure (REE), Physical Activity Energy Expenditure (PAEE), Energy Balance (EB), Excess Postexercise Oxygen Consumption (EPOC), Body Fat Percentage (% BF) and Current Body Composition (CBC).

7. The system of claim 1, wherein the at least one component is further used for storing or transmitting or receiving data of pertinence to the at least one mathematical function by which the physiological status of a subject may be determined.

8. The system of claim 1, further comprising at least one receiver for receiving data from at least one other electronic device, where the data is of pertinence to the at least one mathematical function by which the physiological status of a subject may be determined.

9. The system of claim 1, wherein at least a second component stores, executes, transmits or receives a digital value, at least one mathematical function, at least one parameter of the at least one mathematical function, or any combination thereof for generating at least one value of at least one parameter of physiology for the purpose of further mathematical calculation or for informing the subject of its physiological status.

10. The system of claim 9, wherein the at least one parameter of physiology may be selected from the group consisting of heart rate (HR), breathing rate (BR), hemoglobin concentration ($H_b$), oxyhemoglobin concentration ($H_bO_2$), carbaminohemoglobin concentration ($H_bCO_2$), oxygen saturation (SpO), oxygen consumption rate ($VO_2$), carbon dioxide production rate ($VCO_2$) Respiratory Exchange Ratio (RER), Food Quotient (FQ), Metabolic Fuel Composition (i.e. the macronutrient that a subject is utilizing as metabolic fuel at a given instance), Total Energy Expenditure (TEE), Resting Energy Expenditure (REE), Physical Activity Energy Expenditure (PAEE), Energy Balance (EB), Excess Postexercise Oxygen Consumption (EPOC), Body Fat Percentage (% BF) and Current Body Composition (CBC).

11. The system of claim 1, wherein at least a second component is used for storing or transmitting or receiving data of pertinence to the at least one mathematical function by which the physiological status of a subject may be determined.

12. The system of claim 1, further comprising at least one transmitter for transmitting the at least one value of $VCO_2$ or the at least one value of $VO_2$ to at least one other electronic device for storage, further mathematical processing, analysis, or for informing the subject of its physiological status.

13. The system of claim 7 or 8, wherein the data of pertinence may pertain to the at least one digital signal, at least one mathematical function, at least one parameter, at least one subject input or any combination thereof.

14. The system of claim 1, further comprising at least one power source for powering the system.

15. The system of claim 1, wherein at least one part of the system may be embodied in the form of a wearable device.

16. The system of claim 15, wherein the wearable device comprises a connector for positioning the wearable device on a subject's body, such that the at least one light source and the at least one light detector are positioned in close enough proximity to the subject's skin to allow the at least one light detector to receive light reflected from molecules inside, or in the tissues underlying the subject's skin or on the subject's skin.

17. The system of claim 15, wherein the wearable device comprises a disposable or reusable patch that can be stuck directly onto the skin of the subject.

18. The system of claim 15, wherein the wearable device is incorporated into textiles or other material worn in close proximity to the subject's body.

19. The system of claim 1, wherein $VCO_2$ corresponds to the instantaneous rate of carbon dioxide production by the subject's total aerobic metabolic activity.

20. The system of claim 19, wherein $VCO_2$ is determined from resting and real-time heart rate data measured from the detected signal and at least one mathematical function describing cellular carbon dioxide production rate globally across the subject's whole body, the parameters of which are determined using a parameter estimation approach.

21. The system of claim 1, wherein $VO_2$ corresponds to the instantaneous oxygen consumption rate by the subject's total aerobic metabolic activity.

22. The system of claim 21, wherein $VO_2$ is determined from resting and real-time heart rate data measured from the detected signal and at least one mathematical function describing oxygen consumption rate globally across the subject's whole body, the parameters of which are determined using a parameter estimation approach.

23. A method for transcutaneous measurement of a subject, wherein the method comprises the steps of:
   (a) shining light onto or through tissues of and under skin of the subject;
   (b) receiving light reflected from tissues of the subject's skin or from the tissues underlying the subject's skin and converting the reflected light into a detected signal;
   (c) generating at least one value for each of $VCO_2$ and $VO_2$ from the detected signal, wherein $VO_2$ corresponds to an instantaneous rate of oxygen consumption of the subject and wherein $VCO_2$ corresponds to an instantaneous rate of carbon dioxide production by the subject; and
   (d) continuously calculating a real-time respiratory quotient of the subject from real-time values of $VCO_2$ and $VO_2$ and using the real-time respiratory quotient to determine a real-time energy uptake of the subject.

24. The method of claim 23, wherein the generating step comprises storing, executing, transmitting or receiving a digital value, at least one mathematical function, at least one parameter of the at least one mathematical function, or any combination thereof for generating at least one value of at least one parameter of physiology for the purpose of further mathematical calculation or for informing the subject of its physiological status.

25. The method of claim 23, wherein the generating step stores or transmits or receives data of pertinence to the at least one mathematical function by which the physiological status of a subject may be determined.

26. The method of claim 23, further comprising the step of storing, executing, transmitting or receiving a digital value, at least one mathematical function, at least one parameter of the at least one mathematical function, or any combination thereof for generating at least one value of at least one parameter of physiology for the purpose of further mathematical calculation or for informing the subject of its physiological status.

27. The method of claim 23, wherein the generating step is used for storing or transmitting or receiving data of pertinence to the at least one mathematical function by which the physiological status of a subject may be determined.

28. The method of claim 23, further comprising the step of transmitting the at least one value of $VCO_2$ or the at least one value of $VO_2$ to at least one other electronic device for storage, further mathematical processing, analysis, or for informing the subject of its physiological status.

29. The method of claim 23, further comprising the step of receiving data from at least one other electronic device, where the data is of pertinence to the at least one mathematical function by which the physiological status of a subject may be determined.

30. The method of claim 29, wherein the data of pertinence may pertain to the at least one digital signal, at least one mathematical function, at least one parameter, at least one subject input or any combination thereof.

31. The method of claim 23, where $VCO_2$ corresponds to the instantaneous rate of carbon dioxide production by the subject's total aerobic metabolic activity.

32. The method of claim 31, wherein $VCO_2$ is determined from resting and real-time heart rate data measured from the detected signal and at least one mathematical function describing cellular carbon dioxide production rate globally across the subject's whole body, the parameters of which are determined using a parameter estimation approach.

33. The method of claim 23, wherein $VO_2$ corresponds to the instantaneous oxygen consumption rate by the subject's total aerobic metabolic activity.

34. The method of claim 33, wherein $VO_2$ is determined from resting and real-time heart rate data measured from the detected signal and at least one mathematical function describing oxygen consumption rate globally across the subject's whole body, the parameters of which are determined using a parameter estimation approach.

* * * * *